(12) United States Patent
Collins et al.

(10) Patent No.: US 8,562,346 B2
(45) Date of Patent: *Oct. 22, 2013

(54) DENTAL IMPLANT FOR A JAW WITH REDUCED BONE VOLUME AND IMPROVED OSSEOINTEGRATION FEATURES

(75) Inventors: Michael Collins, San Marcos, CA (US); Jeffrey A. Bassett, Vista, CA (US); Sean Cahill, Temecula, CA (US)

(73) Assignee: Zimmer Dental, Inc., Carlsbad, CA (US)

( * ) Notice: Subject to any disclaimer, the term of this patent is extended or adjusted under 35 U.S.C. 154(b) by 108 days.

This patent is subject to a terminal disclaimer.

(21) Appl. No.: 12/167,049

(22) Filed: Jul. 2, 2008

(65) Prior Publication Data

US 2009/0011384 A1 Jan. 8, 2009

Related U.S. Application Data

(63) Continuation-in-part of application No. 12/065,259, filed as application No. PCT/US2006/033893 on Aug. 30, 2006, now Pat. No. 8,075,312.

(60) Provisional application No. 60/712,577, filed on Aug. 30, 2005.

(51) Int. Cl.
*A61C 8/00* (2006.01)
(52) U.S. Cl.
USPC .......................................................... 433/173
(58) Field of Classification Search
USPC ........................................ 433/173, 174, 175
See application file for complete search history.

(56) References Cited

U.S. PATENT DOCUMENTS

| 1,929,425 A | 10/1933 | Hermann |
| 2,506,845 A | 5/1950 | Randolph |
| 2,721,387 A | 10/1955 | Ashuckian |
| 2,857,670 A | 10/1958 | Kiernan, Jr. |
| 3,314,420 A | 4/1967 | Smith et al. |
| 3,423,830 A | 1/1969 | Halpern et al. |
| 3,423,831 A | 1/1969 | Semmelman |
| 3,497,953 A | 3/1970 | Weissman |
| 3,685,115 A | 8/1972 | Scott |
| 3,713,860 A | 1/1973 | Auskern |

(Continued)

FOREIGN PATENT DOCUMENTS

| AU | 2006284874 B2 | 3/2012 |
| CA | 2506845 | 7/2004 |

(Continued)

OTHER PUBLICATIONS

An Introduction to Silanes and Their Clinical Applications in Dentristry, Jukka P.I Matinlinna et al., vol. 17, No. 2, pp. 155-164 The International Journal of Prosthodontics, 2004.

(Continued)

*Primary Examiner* — Ralph Lewis
(74) *Attorney, Agent, or Firm* — Schwegman, Lundberg & Woessner P.A.

(57) ABSTRACT

A dental implant has a body with a porous metal portion for engaging bone. The porous metal portion has an outer coronal to apical height and an outer diameter. Both the height and diameter are about 4 mm to about 6 mm. This permits the implant to be placed on a jaw with a reduced bone volume.

34 Claims, 8 Drawing Sheets

(56) References Cited

U.S. PATENT DOCUMENTS

| | | | |
|---|---|---|---|
| 3,740,851 A | 6/1973 | Weissman | |
| 3,797,113 A | 3/1974 | Brainin | |
| 3,808,606 A | 5/1974 | Tronzo | |
| 3,849,887 A | 11/1974 | Brainin | |
| 3,851,393 A | 12/1974 | Weiss et al. | |
| 3,896,547 A | 7/1975 | Kulwiec | |
| 3,905,109 A | 9/1975 | Cohen et al. | |
| 3,906,550 A | 9/1975 | Rostoker | |
| 3,919,773 A | 11/1975 | Freeman | |
| 3,934,347 A * | 1/1976 | Lash et al. | 433/173 |
| 3,992,725 A | 11/1976 | Homsy | |
| 4,011,602 A | 3/1977 | Rybicki et al. | |
| 4,016,651 A | 4/1977 | Kawahara et al. | |
| 4,086,701 A | 5/1978 | Kawahara et al. | |
| 4,097,935 A | 7/1978 | Jarcho | |
| 4,122,605 A | 10/1978 | Hirabayashi et al. | |
| 4,131,597 A | 12/1978 | Bluethgen | |
| 4,156,943 A | 6/1979 | Collier | |
| 4,178,686 A | 12/1979 | Riess et al. | |
| 4,195,366 A | 4/1980 | Jarcho et al. | |
| 4,199,864 A | 4/1980 | Ashman | |
| 4,229,170 A | 10/1980 | Perez | |
| 4,244,689 A | 1/1981 | Ashman | |
| 4,252,525 A * | 2/1981 | Child | 433/173 |
| 4,259,072 A * | 3/1981 | Hirabayashi et al. | 433/173 |
| 4,281,991 A | 8/1981 | Michl et al. | |
| 4,283,176 A | 8/1981 | Vajda | |
| 4,321,042 A | 3/1982 | Scheicher | |
| 4,375,967 A | 3/1983 | Schaeffer | |
| 4,379,694 A | 4/1983 | Riess | |
| 4,381,918 A | 5/1983 | Ehmford | |
| 4,411,624 A | 10/1983 | Ogino et al. | |
| 4,431,420 A | 2/1984 | Adair | |
| 4,439,152 A | 3/1984 | Small | |
| 4,448,758 A | 5/1984 | Nagai et al. | |
| 4,475,892 A | 10/1984 | Faunce | |
| 4,478,904 A | 10/1984 | Ducheyne et al. | |
| 4,483,678 A | 11/1984 | Nishio et al. | |
| 4,492,577 A | 1/1985 | Farris et al. | |
| 4,531,915 A | 7/1985 | Tatum, Jr. | |
| 4,531,916 A * | 7/1985 | Scantlebury et al. | 433/173 |
| 4,536,158 A | 8/1985 | Bruins et al. | |
| 4,548,959 A | 10/1985 | Nagai et al. | |
| 4,556,534 A | 12/1985 | Burnett | |
| 4,708,652 A | 11/1987 | Fujiu et al. | |
| 4,713,006 A | 12/1987 | Hakamatsuka et al. | |
| 4,722,688 A | 2/1988 | Lonca | |
| 4,731,085 A | 3/1988 | Koch | |
| 4,737,411 A | 4/1988 | Graves, Jr. et al. | |
| 4,743,260 A | 5/1988 | Burton | |
| 4,744,757 A | 5/1988 | Adair et al. | |
| 4,744,759 A | 5/1988 | Bowen | |
| 4,820,157 A | 4/1989 | Salvo | |
| 4,842,517 A * | 6/1989 | Kawahara et al. | 433/173 |
| 4,871,384 A | 10/1989 | Kasuga | |
| 4,872,839 A | 10/1989 | Brajnovic | |
| 4,872,840 A * | 10/1989 | Bori | 433/173 |
| 4,877,400 A | 10/1989 | Holsclaw | |
| 4,880,610 A | 11/1989 | Constantz | |
| 4,906,190 A | 3/1990 | Michna | |
| 4,909,738 A | 3/1990 | Ai et al. | |
| 4,957,554 A | 9/1990 | Mathers et al. | |
| 4,957,819 A | 9/1990 | Kawahara et al. | |
| 4,959,913 A | 10/1990 | Provence et al. | |
| 4,960,733 A | 10/1990 | Kasuga et al. | |
| 4,969,817 A | 11/1990 | Hiranuma et al. | |
| 4,969,913 A | 11/1990 | Ojima | |
| 4,976,738 A * | 12/1990 | Frey et al. | 623/23.54 |
| 4,983,182 A | 1/1991 | Kijima et al. | |
| 5,000,685 A | 3/1991 | Brajnovic | |
| 5,002,488 A * | 3/1991 | Homsy | 433/169 |
| 5,004,421 A | 4/1991 | Lazarof | |
| 5,007,835 A | 4/1991 | Valen | |
| 5,009,709 A | 4/1991 | Ibsen et al. | |
| 5,049,074 A * | 9/1991 | Otani et al. | 433/173 |
| 5,055,497 A | 10/1991 | Okada et al. | |
| 5,061,285 A | 10/1991 | Koch | |
| 5,062,798 A | 11/1991 | Tsuge et al. | |
| 5,064,731 A | 11/1991 | Miyazaki et al. | |
| 5,076,789 A | 12/1991 | Tanaka | |
| 5,087,200 A | 2/1992 | Brajnovic et al. | |
| 5,120,340 A | 6/1992 | Ducheyne et al. | |
| 5,123,844 A | 6/1992 | Wakai et al. | |
| 5,125,839 A | 6/1992 | Ingber et al. | |
| 5,125,971 A | 6/1992 | Nonami et al. | |
| 5,139,424 A | 8/1992 | Yli-Urpo | |
| 5,152,687 A | 10/1992 | Amino | |
| 5,176,747 A | 1/1993 | Panzera et al. | |
| 5,180,303 A | 1/1993 | Homburg et al. | |
| 5,186,626 A | 2/1993 | Tanaka | |
| 5,192,325 A | 3/1993 | Kijima et al. | |
| 5,194,000 A | 3/1993 | Dury | |
| 5,194,001 A | 3/1993 | Salvo | |
| 5,199,873 A | 4/1993 | Schulte et al. | |
| 5,205,745 A | 4/1993 | Kamiya et al. | |
| D336,683 S | 6/1993 | Inoue et al. | |
| 5,232,365 A | 8/1993 | Ikehara | |
| 5,232,878 A | 8/1993 | Kasuga et al. | |
| 5,236,458 A | 8/1993 | Ducheyne et al. | |
| 5,238,405 A | 8/1993 | Marlin | |
| 5,254,005 A * | 10/1993 | Zuest | 433/173 |
| 5,282,861 A * | 2/1994 | Kaplan | 623/23.51 |
| 5,282,863 A | 2/1994 | Burton | |
| 5,288,232 A | 2/1994 | Panzera et al. | |
| 5,306,673 A | 4/1994 | Hermansson et al. | |
| 5,308,391 A | 5/1994 | Komma et al. | |
| 5,310,343 A | 5/1994 | Hasegawa et al. | |
| 5,312,254 A | 5/1994 | Rosenlicht | |
| 5,314,334 A | 5/1994 | Panzera et al. | |
| 5,342,201 A | 8/1994 | Oden | |
| 5,344,318 A | 9/1994 | Wilson et al. | |
| 5,344,457 A | 9/1994 | Pilliar et al. | |
| 5,346,397 A | 9/1994 | Braiman | |
| 5,415,546 A | 5/1995 | Cox, Sr. | |
| 5,419,702 A | 5/1995 | Beaty et al. | |
| 5,425,639 A | 6/1995 | Anders | |
| 5,425,640 A | 6/1995 | Scharf | |
| 5,439,380 A | 8/1995 | Marlin | |
| 5,443,515 A | 8/1995 | Cohen et al. | |
| 5,449,291 A | 9/1995 | Lueschen et al. | |
| 5,458,488 A | 10/1995 | Chalifoux | |
| 5,468,544 A | 11/1995 | Marcolongo et al. | |
| 5,476,383 A | 12/1995 | Beaty et al. | |
| 5,549,123 A | 8/1996 | Okuyama et al. | |
| 5,554,665 A | 9/1996 | Tateosian et al. | |
| 5,562,733 A | 10/1996 | Weissbach et al. | |
| 5,571,016 A | 11/1996 | Ingber et al. | |
| 5,572,652 A | 11/1996 | Robusto et al. | |
| 5,575,652 A | 11/1996 | Gaffar et al. | |
| 5,584,693 A | 12/1996 | Nishihara | |
| 5,591,030 A | 1/1997 | Thiel et al. | |
| 5,612,049 A | 3/1997 | Li et al. | |
| 5,614,330 A | 3/1997 | Panzera et al. | |
| 5,621,035 A | 4/1997 | Lyles et al. | |
| 5,624,262 A | 4/1997 | Yarovesky et al. | |
| 5,636,989 A | 6/1997 | Somborac | |
| 5,645,934 A | 7/1997 | Marcolongo et al. | |
| 5,674,069 A | 10/1997 | Osorio | |
| 5,676,745 A | 10/1997 | Kelly et al. | |
| 5,683,249 A | 11/1997 | Ibsen et al. | |
| 5,685,714 A | 11/1997 | Beaty et al. | |
| 5,695,337 A | 12/1997 | Tyszbiat Sadoun | |
| 5,697,785 A | 12/1997 | Delahaye | |
| 5,697,976 A | 12/1997 | Chesterfield et al. | |
| 5,697,997 A | 12/1997 | Aronsson et al. | |
| 5,698,019 A | 12/1997 | Frank et al. | |
| 5,702,346 A * | 12/1997 | Lazzara et al. | 433/173 |
| 5,713,994 A | 2/1998 | Kramer et al. | |
| 5,723,007 A | 3/1998 | Engel et al. | |
| 5,727,943 A | 3/1998 | Beaty et al. | |
| 5,755,809 A | 5/1998 | Cohen et al. | |
| 5,759,036 A | 6/1998 | Hinds | |
| 5,762,500 A | 6/1998 | Lazarof | |
| 5,772,438 A | 6/1998 | Deom | |

(56) References Cited

U.S. PATENT DOCUMENTS

| | | |
|---|---|---|
| 5,775,912 A | 7/1998 | Panzera et al. |
| 5,785,524 A | 7/1998 | Wolf |
| 5,833,463 A | 11/1998 | Hurson |
| 5,833,464 A | 11/1998 | Foser |
| 5,839,900 A | 11/1998 | Billet et al. |
| 5,843,348 A | 12/1998 | Giordano |
| 5,849,068 A | 12/1998 | Hofmann, geb. Roth et al. |
| 5,873,721 A | 2/1999 | Willoughby |
| 5,910,273 A | 6/1999 | Thiel et al. |
| 5,915,967 A | 6/1999 | Clokie |
| 5,925,180 A | 7/1999 | Frank et al. |
| 5,931,674 A | 8/1999 | Hanosh et al. |
| 5,934,906 A | 8/1999 | Phimmasone |
| 5,939,211 A | 8/1999 | Mormann |
| 5,947,732 A | 9/1999 | Beaty et al. |
| 5,947,737 A | 9/1999 | Billet et al. |
| 5,947,893 A | 9/1999 | Agrawal et al. |
| 5,951,290 A | 9/1999 | Ardizio et al. |
| 5,951,293 A | 9/1999 | Billet et al. |
| 5,951,295 A | 9/1999 | Lyles et al. |
| 5,961,328 A | 10/1999 | Somborac et al. |
| 5,964,592 A | 10/1999 | Hites et al. |
| 5,971,760 A | 10/1999 | Letcher |
| 5,975,905 A | 11/1999 | Kim et al. |
| 5,984,683 A | 11/1999 | Sakata et al. |
| 5,989,026 A | 11/1999 | Rogers et al. |
| 5,989,027 A | 11/1999 | Wagner et al. |
| 6,010,337 A | 1/2000 | Billet et al. |
| 6,012,923 A | 1/2000 | Bassett et al. |
| 6,013,591 A | 1/2000 | Ying et al. |
| 6,027,742 A | 2/2000 | Lee et al. |
| 6,039,568 A | 3/2000 | Hinds |
| 6,045,361 A | 4/2000 | Misch et al. |
| 6,048,203 A | 4/2000 | Rosenberg |
| 6,048,205 A | 4/2000 | Wright |
| 6,054,400 A | 4/2000 | Brink et al. |
| RE36,689 E | 5/2000 | Beaty et al. |
| 6,056,547 A | 5/2000 | Names |
| 6,063,442 A | 5/2000 | Cohen et al. |
| 6,080,692 A | 6/2000 | Reise et al. |
| 6,087,553 A | 7/2000 | Cohen et al. |
| 6,117,456 A | 9/2000 | Lee et al. |
| 6,120,293 A | 9/2000 | Lazzara et al. |
| 6,126,445 A | 10/2000 | Willoughby |
| 6,126,732 A | 10/2000 | Hofmann et al. |
| 6,135,775 A | 10/2000 | Weisman |
| 6,146,423 A | 11/2000 | Cohen et al. |
| 6,152,737 A | 11/2000 | Beaty et al. |
| 6,159,010 A | 12/2000 | Rogers et al. |
| 6,159,417 A | 12/2000 | Giordano |
| 6,168,435 B1 | 1/2001 | Beaty et al. |
| 6,168,436 B1 | 1/2001 | O'Brien |
| 6,168,633 B1 | 1/2001 | Shoher et al. |
| 6,183,256 B1 | 2/2001 | Fisher et al. |
| 6,183,515 B1 | 2/2001 | Barlow et al. |
| 6,186,791 B1 | 2/2001 | Karmaker et al. |
| 6,193,516 B1 | 2/2001 | Story |
| 6,200,137 B1 | 3/2001 | Holand et al. |
| 6,206,192 B1 | 3/2001 | Winstead et al. |
| 6,214,368 B1 | 4/2001 | Lee et al. |
| 6,224,662 B1 | 5/2001 | Nemeth |
| 6,227,857 B1 * | 5/2001 | Morgan et al. ............... 433/173 |
| 6,244,869 B1 | 6/2001 | Billet et al. |
| 6,250,922 B1 | 6/2001 | Bassett et al. |
| 6,267,597 B1 | 7/2001 | Kim |
| 6,270,347 B1 | 8/2001 | Webster et al. |
| 6,271,282 B1 | 8/2001 | Giordano |
| 6,280,863 B1 | 8/2001 | Frank et al. |
| 6,283,753 B1 | 9/2001 | Willoughby |
| 6,287,341 B1 | 9/2001 | Lee et al. |
| 6,299,448 B1 * | 10/2001 | Zdrahala et al. ............. 433/173 |
| 6,306,784 B1 | 10/2001 | Drescher et al. |
| 6,322,728 B1 | 11/2001 | Brodkin et al. |
| 6,325,628 B1 | 12/2001 | Morgan |
| 6,331,312 B1 | 12/2001 | Lee et al. |
| 6,342,302 B1 | 1/2002 | Steidl et al. |
| 6,342,458 B1 | 1/2002 | Schweiger et al. |
| 6,343,930 B1 | 2/2002 | Beaty et al. |
| 6,345,984 B2 | 2/2002 | Karmaker et al. |
| 6,354,836 B1 | 3/2002 | Panzera et al. |
| 6,362,250 B1 | 3/2002 | Karmaker et al. |
| 6,362,251 B1 | 3/2002 | Alkemper et al. |
| 6,379,153 B1 | 4/2002 | Schroering |
| 6,386,876 B1 | 5/2002 | Lee |
| 6,394,806 B1 | 5/2002 | Kumar |
| 6,402,517 B1 | 6/2002 | Hozumi et al. |
| 6,419,491 B1 | 7/2002 | Ricci et al. |
| 6,431,868 B2 | 8/2002 | Story |
| 6,439,890 B1 | 8/2002 | Karmaker et al. |
| 6,447,549 B1 | 9/2002 | Taft |
| 6,450,813 B1 | 9/2002 | McDonald et al. |
| 6,451,292 B2 | 9/2002 | Warford, III et al. |
| 6,454,569 B1 | 9/2002 | Hollander et al. |
| 6,485,849 B2 | 11/2002 | Petticrew |
| 6,495,073 B2 | 12/2002 | Bodenmiller et al. |
| 6,497,573 B2 | 12/2002 | Wagner et al. |
| 6,503,625 B1 | 1/2003 | Rieder et al. |
| 6,514,453 B2 | 2/2003 | Vigliotti et al. |
| 6,527,553 B2 | 3/2003 | Yeung |
| 6,540,784 B2 | 4/2003 | Barlow et al. |
| 6,627,327 B2 | 9/2003 | Reidt et al. |
| 6,641,775 B2 | 11/2003 | Vigliotti et al. |
| 6,648,645 B1 | 11/2003 | MacDougald et al. |
| 6,666,684 B1 | 12/2003 | Names |
| 6,669,476 B2 | 12/2003 | Prestipino et al. |
| 6,679,701 B1 | 1/2004 | Blacklock |
| 6,689,202 B2 | 2/2004 | Panzera |
| 6,743,936 B1 | 6/2004 | Wellinghoff et al. |
| 6,752,863 B2 | 6/2004 | Lyles et al. |
| 6,755,651 B2 | 6/2004 | Brodbeck |
| 6,787,584 B2 | 9/2004 | Jia et al. |
| 6,797,006 B2 | 9/2004 | Hodorek |
| 6,808,659 B2 | 10/2004 | Schulman et al. |
| 6,821,462 B2 | 11/2004 | Schulman et al. |
| 6,846,181 B2 | 1/2005 | Karmaker et al. |
| 6,878,456 B2 | 4/2005 | Castro et al. |
| 6,881,488 B2 | 4/2005 | Giordano |
| 6,932,606 B2 | 8/2005 | Aravena et al. |
| 6,945,448 B2 | 9/2005 | Medlin et al. |
| 6,949,251 B2 | 9/2005 | Dalal et al. |
| 6,953,594 B2 | 10/2005 | Lee et al. |
| 6,976,998 B2 | 12/2005 | Rizzo |
| 6,976,999 B2 | 12/2005 | Charlebois et al. |
| 6,984,261 B2 | 1/2006 | Cummings et al. |
| 6,986,660 B2 | 1/2006 | Kumar et al. |
| 7,011,522 B2 | 3/2006 | Panzera et al. |
| 7,291,012 B2 | 11/2007 | Lyren |
| 7,718,100 B2 | 5/2010 | Soler et al. |
| 8,075,312 B2 | 12/2011 | Collins et al. |
| 2001/0000486 A1 | 4/2001 | Story |
| 2001/0051832 A1 | 12/2001 | Bakker et al. |
| 2002/0028424 A1 | 3/2002 | Prestipino et al. |
| 2002/0039718 A1 | 4/2002 | Kwan |
| 2002/0076673 A1 | 6/2002 | Wagner et al. |
| 2002/0095213 A1 | 7/2002 | Bakker et al. |
| 2002/0115742 A1 | 8/2002 | Trieu et al. |
| 2002/0155412 A1 | 10/2002 | Panzera et al. |
| 2002/0160334 A1 | 10/2002 | Brodbeck |
| 2003/0031984 A1 | 2/2003 | Rusin et al. |
| 2003/0068598 A1 | 4/2003 | Vallittu et al. |
| 2003/0073394 A1 | 4/2003 | Reidt et al. |
| 2003/0087984 A1 | 5/2003 | Erbe et al. |
| 2003/0096214 A1 | 5/2003 | Luthardt et al. |
| 2003/0134925 A1 | 7/2003 | Guzauskas |
| 2003/0148247 A1 | 8/2003 | Sicurelli et al. |
| 2004/0024081 A1 | 2/2004 | Trieu et al. |
| 2004/0058299 A1 | 3/2004 | Molin et al. |
| 2004/0064192 A1 | 4/2004 | Bubb |
| 2004/0097627 A1 | 5/2004 | Vallittu et al. |
| 2004/0106085 A1 | 6/2004 | Vallittu et al. |
| 2004/0106087 A1 | 6/2004 | Weigl et al. |
| 2004/0131562 A1 | 7/2004 | Gower et al. |
| 2004/0152034 A1 | 8/2004 | Cummings et al. |
| 2004/0170946 A1 * | 9/2004 | Lyren ........................... 433/173 |

(56) References Cited

U.S. PATENT DOCUMENTS

| | | |
|---|---|---|
| 2004/0185420 A1 | 9/2004 | Schulter |
| 2004/0197737 A1 | 10/2004 | Uckelmann et al. |
| 2004/0234925 A1 | 11/2004 | Benhamou |
| 2004/0241614 A1 | 12/2004 | Goldberg et al. |
| 2005/0008990 A1 | 1/2005 | Ganz et al. |
| 2005/0014108 A1 | 1/2005 | Wohrle et al. |
| 2005/0023710 A1 | 2/2005 | Brodkin et al. |
| 2005/0028424 A1 | 2/2005 | Poinski |
| 2005/0031704 A1 | 2/2005 | Ahn |
| 2005/0084533 A1 | 4/2005 | Howdle et al. |
| 2005/0084819 A1 | 4/2005 | Sims et al. |
| 2005/0084821 A1 | 4/2005 | Sims et al. |
| 2005/0096652 A1 | 5/2005 | Burton |
| 2005/0100724 A1 | 5/2005 | Seargeant |
| 2005/0109060 A1 | 5/2005 | Cummings et al. |
| 2005/0123672 A1 | 6/2005 | Justin et al. |
| 2005/0184134 A1 | 8/2005 | Charlebois et al. |
| 2005/0191248 A1 | 9/2005 | Hunter et al. |
| 2005/0221259 A1 | 10/2005 | Anderson |
| 2005/0261795 A1 | 11/2005 | Ghosh et al. |
| 2005/0266382 A1 | 12/2005 | Soler et al. |
| 2006/0075826 A1 | 4/2006 | Roberts et al. |
| 2006/0105295 A1 | 5/2006 | Mayer et al. |
| 2007/0015110 A1 | 1/2007 | Zhang |
| 2007/0111165 A1 | 5/2007 | Wallick |
| 2007/0118221 A1 | 5/2007 | Robie et al. |
| 2007/0148621 A1 | 6/2007 | Yakir |
| 2007/0184265 A1 | 8/2007 | Ranganathan et al. |
| 2008/0050699 A1 | 2/2008 | Zhang |
| 2008/0241793 A1 | 10/2008 | Collins |
| 2008/0280254 A1 | 11/2008 | Ackermann |
| 2009/0036908 A1 | 2/2009 | Zokol et al. |
| 2009/0093888 A1 | 4/2009 | Dawson et al. |
| 2009/0098510 A1 | 4/2009 | Zhang |
| 2009/0098511 A1 | 4/2009 | Zhang |

FOREIGN PATENT DOCUMENTS

| | | |
|---|---|---|
| DE | 3110694 A1 | 9/1982 |
| DE | 4209569 | 11/1994 |
| DE | 19508224 A1 | 9/1995 |
| DE | 19529036 | 3/1997 |
| DE | 10105398 | 8/2010 |
| EP | 0266313 | 5/1988 |
| EP | 0345581 | 12/1989 |
| EP | 0366018 | 5/1990 |
| EP | 0417018 | 3/1991 |
| EP | 0467948 | 1/1992 |
| EP | 0498923 | 8/1992 |
| EP | 0333503 | 2/1993 |
| EP | 0560279 | 9/1993 |
| EP | 0806211 | 11/1997 |
| EP | 0271236 | 6/1998 |
| EP | 0950421 | 10/1999 |
| EP | 1281372 | 2/2003 |
| EP | 1598028 | 11/2005 |
| EP | 1712205 | 10/2006 |
| FR | 2796265 | 1/2001 |
| GB | 701802 A | 1/1954 |
| GB | 1526780 | 9/1978 |
| GB | 2199626 A | 7/1988 |
| GB | 2401867 | 11/2004 |
| GB | 2416996 | 2/2006 |
| JP | 61275205 A | 12/1986 |
| JP | 61275305 | 12/1986 |
| JP | 1025849 | 1/1989 |
| JP | 7255832 A | 10/1995 |
| JP | 9313505 A | 12/1997 |
| JP | 63290559 | 11/1998 |
| JP | 2000501966 A | 2/2000 |
| JP | 2002126071 | 5/2002 |
| WO | WO-8604807 A1 | 8/1986 |
| WO | 8900410 | 1/1989 |
| WO | 9011979 | 11/1990 |
| WO | 9320773 | 10/1993 |
| WO | 9421190 | 9/1994 |
| WO | 9528973 | 11/1995 |
| WO | 9721393 | 6/1997 |
| WO | WO-9722308 A1 | 6/1997 |
| WO | 9741809 | 11/1997 |
| WO | 9830170 | 7/1998 |
| WO | 0021455 | 4/2000 |
| WO | 0132072 | 5/2001 |
| WO | 0187193 | 5/2001 |
| WO | 0187193 | 11/2001 |
| WO | 0236039 | 5/2002 |
| WO | WO 02/34155 | * 5/2002 |
| WO | 02062901 | 8/2002 |
| WO | 02064100 | 8/2002 |
| WO | 03065939 | 8/2003 |
| WO | 03065996 | 8/2003 |
| WO | 03078508 | 9/2003 |
| WO | 03094774 | 11/2003 |
| WO | 2004054464 | 7/2004 |
| WO | 2004103202 | 12/2004 |
| WO | WO-2006082610 A2 | 8/2006 |
| WO | 2007027794 | 3/2007 |
| WO | 2007086832 | 8/2007 |
| WO | WO-2009029711 A1 | 3/2009 |
| WO | WO-2009029718 A1 | 3/2009 |
| WO | WO-2009032759 A1 | 3/2009 |
| WO | WO-2009032766 A1 | 3/2009 |
| WO | WO-2010002661 A2 | 1/2010 |
| WO | WO-2010002661 A3 | 1/2010 |

OTHER PUBLICATIONS

Computer-Guided Immediate Provisionalization of Anterior Multiple Adjacent Implants: Surgical and Prosthodontic Rationale, Joseph Y. K. Kan, Practical Procedures & Aethetic Dentistry. vol. 18, No. 10, 617-623, 2006.

Flocculants, Binders, and Bonds, Chapter 11, Molecular Binders pp. 173-177, 1995.

Innovative Ceramic-Fiber Technology Energizes Advanced Cerametrics, Richard B. Cass et al. Story—the American Ceramic Society, American Ceramics Society Bulletin, Nov. 2003, pp. 9701-9706.

PEEK-CLASSIX, Information Sheet Invibio Ltd., Properties of PEEK-CLASSIX White Granular, Nov. 2003.

Presurgical Planning With CT-Derived Fabrication of Surgical Guides, Scott D. Ganz, J Oral Maxillofac Surg 63:59-73, 2005, Suppl 2.

Prosthetically Directed Implant Placement ing Computer Software to Ensure Precise Placement and Predictable Prosthetic Outcomes. Part 1: Diagnostics, Imaging, and Collaborative Accountability, Alan L. Rosenfeld, International Journal of Periodontics & Restorative Dentistry, vol. 26, No. 3, 2006, 215-221.

Shape Optimization of Randomly Oriented Short Fibers for Bone Cement Reinforcements, Yan Zhou, Chaodi Li, James J. Mason, Materials Science & Engineering A 393 (2005) 374-381.

The Clinical Assessment of a Ceramic-Coated Transmucosal Dental Implant Collar; International Journal of Prosthodonics; 1996—vol. 9, Issue 5; pp. 466-472.

Two Applications of Transmucosal Milled Ceramic in Implantology; Preliminary Clinical Examples; Implant Quintessence Dentistry International; Aug. t 1996—vol. 27, Issue 8, pp. 533-547.

International Search Report from related application PCT/ 2006/033893, dated Jan. 29, 2007, 1 page.

International Search Report from related application PCT/ 2006/020130, dated Feb. 6, 2007, 10 pages.

International Search Report from related application PCT/ 2007/069562, dated Jul. 7, 2008, 1 page.

International Search Report from related application PCT/ 2008/074616; dated Dec. 16, 2008; 4 pages.

International Search Report from related application PCT/ 2008/074645, dated Dec. 29, 2008; 9 pages.

International Search Report from related application PCT/ 2008/074642; dated Feb. 12, 2009, 4 pages.

(56) References Cited

OTHER PUBLICATIONS

International Search Report from related application PCT/ 2008/ 074655; dated Feb. 18, 2009, 9 pages.
International Search Report from related application PCT/ 2009/ 048469, dated Oct. 19, 2009, 9 pages.
International Search Report from related application PCT/ 2009/ 048476; dated Dec. 10, 2009; 13 pages.
International Search Report from related application PCT/ 2009/ 048481; dated Dec. 10, 2009; 13 pages.
International Search Report from related application PCT/ 2009/ 062308; dated Jan. 21, 2010; 17 pages.
International Search Report from related application PCT/ 2009/ 048456; dated Apr. 27, 2010; 5 pages.
"U.S. Appl. No. 11/847,476, Final Office Action mailed Jul. 13, 2012", 7 pgs.
"U.S. Appl. No. 11/847,476, Examiners Interview Summary mailed Nov. 14, 2012", 3 pgs.
"U.S. Appl. No. 11/847,476, Final Office Action mailed Dec. 8, 2010", 7 pgs.
"U.S. Appl. No. 11/847,476, Non Final Office Action mailed Jan. 26, 2012", 6 pgs.
"U.S. Appl. No. 11/847,476, Non Final Office Action mailed Jun. 24, 2010", 7 pgs.
"U.S. Appl. No. 11/847,476, Non Final Office Action mailed Jul. 11, 2011", 8 pgs.
"U.S. Appl. No. 11/847,476, Response filed Apr. 8, 2011 to Final Office Action mailed Dec. 8, 2010", 15 pgs.
"U.S. Appl. No. 11/847,476, Response filed Apr. 26, 2012 to Non Final Office Action mailed Jan. 26, 2012", 12 pgs.
"U.S. Appl. No. 11/847,476, Response filed Apr. 29, 2010 to Restriction Requirement mailed Mar. 29, 2010", 2 pgs.
"U.S. Appl. No. 11/847,476, Response filed Sep. 17, 2010 to Non Final Office Action mailed Jun. 24, 2010", 12 pgs.
"U.S. Appl. No. 11/847,476, Response filed Nov. 10, 2011 to Non Final Office Action mailed Jul. 11, 2011", 12 pgs.
"U.S. Appl. No. 11/847,476, Restriction Requirement mailed Mar. 29, 2010", 9 pgs.
"U.S. Appl. No. 12/065,259, Final Office Action mailed Dec. 9, 2010", 8 pgs.
"U.S. Appl. No. 12/065,259, Non Final Office Action mailed Apr. 27, 2011", 8 pgs.
"U.S. Appl. No. 12/065,259, Non Final Office Action mailed Dec. 21, 2009", 8 pgs.
"U.S. Appl. No. 12/065,259, Notice of Allowance mailed Sep. 16, 2011", 7 pgs.
"U.S. Appl. No. 12/065,259, Response filed Apr. 7, 2011 to Final Office Action mailed Dec. 9, 2010", 10 pgs.
"U.S. Appl. No. 12/065,259, Response filed Jun. 18, 2010 to Non Final Office Action mailed Dec. 21, 2009", 9 pgs.
"U.S. Appl. No. 12/065,259, Response filed Jun. 30, 2011 to Non Final Office Action mailed Apr. 27, 2011", 8 pgs.
"U.S. Appl. No. 12/065,259, Response filed Sep. 30, 2010 to Restriction Requirement mailed Aug. 31, 2010", 7 pgs.
"U.S. Appl. No. 12/065,259, Restriction Requirement mailed Aug. 31, 2010", 5 pgs.
"U.S. Appl. No. 12/167,004, Examiner Interview Summary mailed Mar. 2, 2012", 3 pgs.
"U.S. Appl. No. 12/167,004, Final Office Action mailed Nov. 9, 2011", 16 pgs.
"U.S. Appl. No. 12/167,004, Non Final Office Action mailed Feb. 13, 2012", 17 pgs.
"U.S. Appl. No. 12/167,004, Non Final Office Action mailed May 24, 2011", 17 pgs.
"U.S. Appl. No. 12/167,004, Non Final Office Action mailed Nov. 10, 2010", 12 pgs.
"U.S. Appl. No. 12/167,004, Response filed Feb. 9, 2012 to Final Office Action mailed Nov. 9, 2011", 15 pgs.
"U.S. Appl. No. 12/167,004, Response filed Mar. 10, 2011 to Non Final Office Action mailed Nov. 10, 2010", 14 pgs.
"U.S. Appl. No. 12/167,004, Response filed Aug. 24, 2011 to Non Final Office Action mailed May 24, 2011", 13 pgs.
"U.S. Appl. No. 12/167,004, Response filed Oct. 11, 2010 to Restriction Requirement mailed Sep. 14, 2010", 6 pgs.
"U.S. Appl. No. 12/167,004, Restriction Requirement mailed Sep. 14, 2010", 4 pgs.
"U.S. Appl. No. 12/167,018, Examiner Interview Summary mailed Oct. 23, 2012", 3 pgs.
"U.S. Appl. No. 12/167,018, Final Office Action mailed May 23, 2011", 22 pgs.
"U.S. Appl. No. 12/167,018, Final Office Action mailed Jun. 14, 2012", 19 pgs.
"U.S. Appl. No. 12/167,018, Non Final Office Action mailed Aug. 30, 2011", 20 pgs.
"U.S. Appl. No. 12/167,018, Non Final Office Action mailed Nov. 18, 2010", 22 pgs.
"U.S. Appl. No. 12/167,018, Response filed Mar. 18, 2011 to Non Final Office Action mailed Nov. 18, 2010", 11 pgs.
"U.S. Appl. No. 12/167,018, Response filed Aug. 23, 2011 to Final Office Action mailed May 23, 2011", 11 pgs.
"U.S. Appl. No. 12/167,018, Response filed Oct. 27, 2010 to Restriction Requirement mailed Aug. 30, 2010", 6 pgs.
"U.S. Appl. No. 12/167,018, Response filed Nov. 9, 2012 to Final Office Action mailed Jun. 14, 2012", 17 pgs.
"U.S. Appl. No. 12/167,018, Response filed Nov. 22, 2011 to Non Final Office Action mailed Aug. 30, 2011", 10 pgs.
"U.S. Appl. No. 12/167,018, Restriction Requirement mailed Aug. 30, 2010", 6 pgs.
"U.S. Appl. No. 12/167,032, Examiner Interview Summary mailed Oct. 23, 2012", 3 pgs.
"U.S. Appl. No. 12/167,032, Final Office Action mailed Apr. 27, 2011", 17 pgs.
"U.S. Appl. No. 12/167,032, Final Office Action mailed Jun. 19, 2012", 14 pgs.
"U.S. Appl. No. 12/167,032, Non Final Office Action mailed Sep. 9, 2011", 14 pgs.
"U.S. Appl. No. 12/167,032, Non Final Office Action mailed Oct. 21, 2010", 16 pgs.
"U.S. Appl. No. 12/167,032, Response filed Feb. 17, 2011 to Non Final Office Action mailed Oct. 21, 2010", 10 pgs.
"U.S. Appl. No. 12/167,032, Response filed Aug. 29, 2011 to Final Office Action mailed Apr. 27, 2011", 9 pgs.
"U.S. Appl. No. 12/167,032, Response filed Sep. 30, 2010 to Restriction Requirement mailed Sep. 1, 2010", 6 pgs.
"U.S. Appl. No. 12/167,032, Response filed Nov. 9, 2012 to Final Office Action mailed Jun. 19, 2012", 11 pgs.
"U.S. Appl. No. 12/167,032, Response filed Nov. 22, 2011 to Non Final Office Action mailed Sep. 9, 2011", 8 pgs.
"U.S. Appl. No. 12/167,032, Restriction Requirement mailed Sep. 1, 2010", 6 pgs.
"Canadian Application Serial No. 2,620,427,Office Action mailed Jan. 7, 2013", 3 pgs.
"European Application Serial No. 06813974.0, European Search Report mailed Jan. 12, 2010", 5 pgs.
"European Application Serial No. 06813974.0, Office Action mailed Apr. 8, 2008", 2 pgs.
"European Application Serial No. 06813974.0, Office Action mailed Apr. 14, 2010", 1 pg.
"European Application Serial No. 06813974.0, Response filed Oct. 21, 2010 to Office Action mailed Apr. 14, 2010", 17 pgs.
"European Application Serial No. 08828199.3, Office Action mailed May 11, 2010", 2 pgs.
"European Application Serial No. 08828199.3, Response filed Jun. 18, 2010 to Office Action mailed May 11, 2010", 9 pgs.
"European Application Serial No. 08828675.2, Office Action mailed May 11, 2010", 2 pgs.
"European Application Serial No. 08828675.2, Response filed Jun. 17, 2010 to Office Action mailed May 11, 2010", 2 pgs.
"European Application Serial No. 09774112.8, Office Action mailed Feb. 17, 2011", 2 pgs.
"European Application Serial No. 09774112.8, Office Action mailed Mar. 16, 2011", 1 pg.

(56) References Cited

OTHER PUBLICATIONS

"European Application Serial No. 09774112.8, Response filed Mar. 28, 2011 to Office Action mailed Feb. 17, 2011", 6 pgs.

"International Application Serial No. PCT/US2006/033893, International Preliminary Report on Patentability mailed Mar. 4, 2008", 4 pgs.

"International Application Serial No. PCT/US2006/033893, Written Opinion mailed Jan. 29, 2007", 3 pgs.

"International Application Serial No. PCT/US2008/074616, International Preliminary Report on Patentability mailed Mar. 2, 2010", 6 pgs.

"International Application Serial No. PCT/US2008/074616, Written Opinion mailed Dec. 16, 2008", 5 pgs.

"International Application Serial No. PCT/US2008/074642, International Preliminary Report on Patentability mailed Mar. 2, 2010", 5 pgs.

"International Application Serial No. PCT/US2008/074642, Written Opinion mailed Feb. 12, 2009", 4 pgs.

"International Application Serial No. PCT/US2008/074645, International Preliminary Report on Patentability mailed Mar. 2, 2010", 6 pgs.

"International Application Serial No. PCT/US2008/074645, Written Opinion mailed Dec. 29, 2008", 5 pgs.

"International Application Serial No. PCT/US2008/074655, International Preliminary Report on Patentability mailed Mar. 2, 2010", 6 pgs.

"International Application Serial No. PCT/US2008/074655, Written Opinion mailed Feb. 18, 2009", 5 pgs.

"International Application Serial No. PCT/US2009/048456, International Preliminary Report on Patentability mailed Jan. 5, 2011", 7 pgs.

"International Application Serial No. PCT/US2009/048456, Written Opinion mailed Apr. 27, 2010", 6 pgs.

"International Application Serial No. PCT/US2009/048476, Written Opinion mailed Dec. 10, 2009", 6 pgs.

"International Application Serial No. PCT/US2009/048481, Written Opinion mailed Dec. 10, 2009", 7 pgs.

"Japanese Application Serial No. 2008-529238, Response filed Mar. 29, 2013 to Office Action mailed Oct. 23, 2012", (W/ English Translation), 7 pgs.

"Japanese Application Serial No. 2008-529238, Office Action mailed Jan. 10, 2012", (W/ English Translation), 4 pgs.

"Japanese Application Serial No. 2008-529238, Office Action mailed Oct. 23, 2012", (W/ English Translation), 11 pgs.

"Japanese Application Serial No. 2008-529238, Response filed Apr. 2012 to Office Action mailed Jan. 10, 2012", (W/ English Translation), 9 pgs.

\* cited by examiner

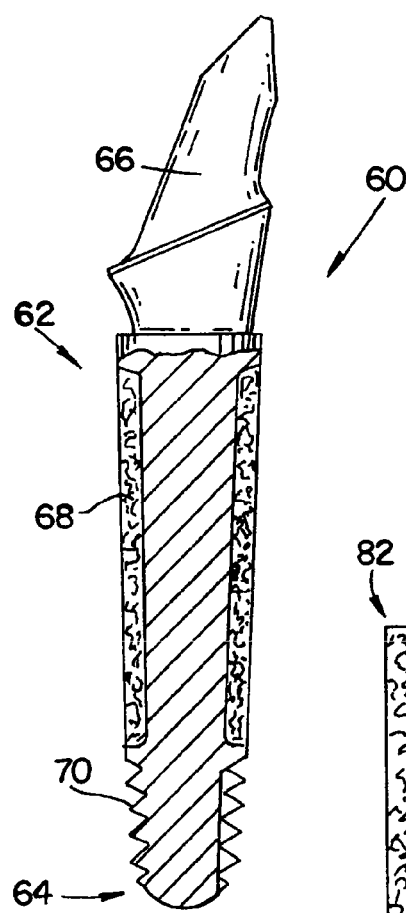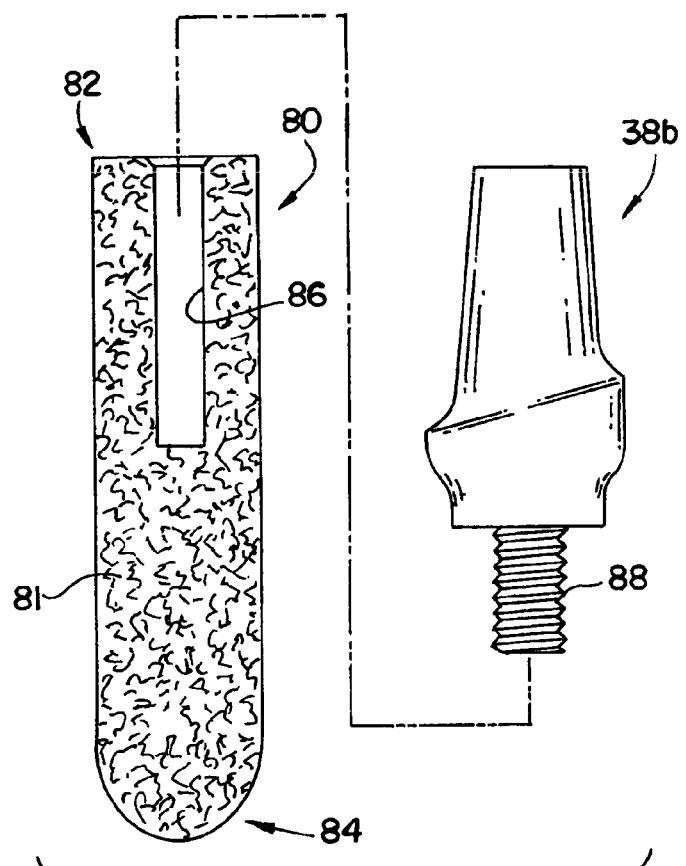

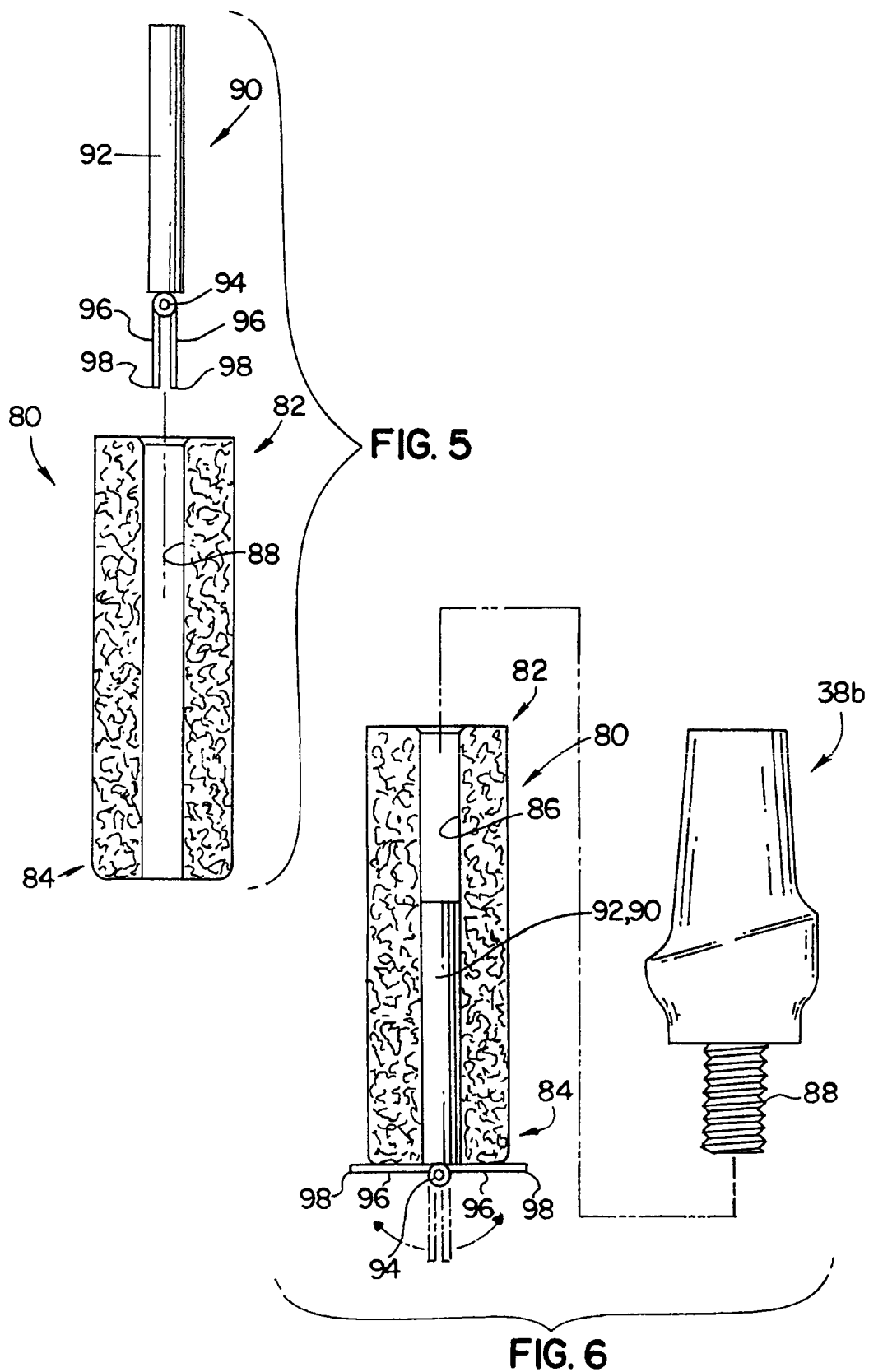

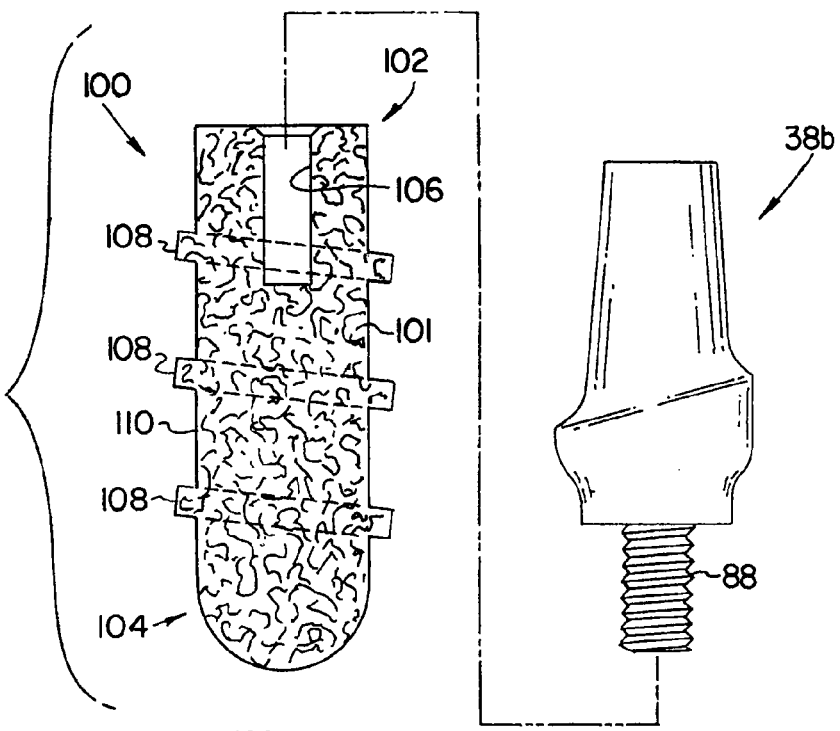
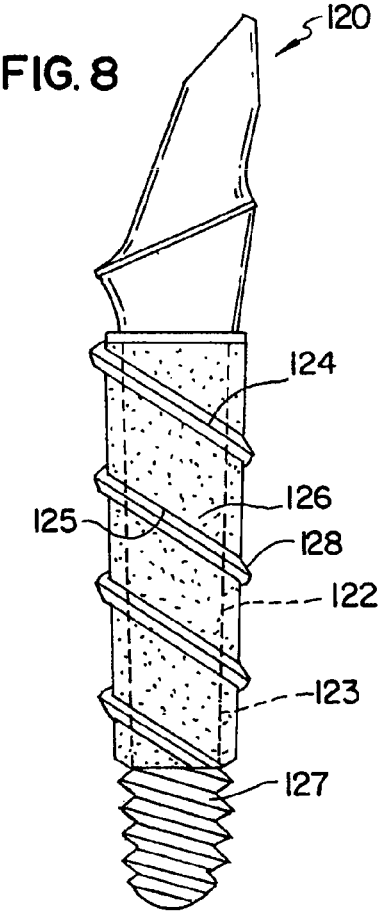
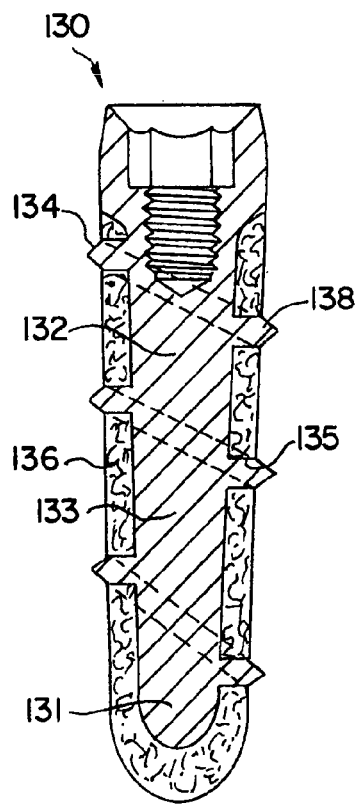

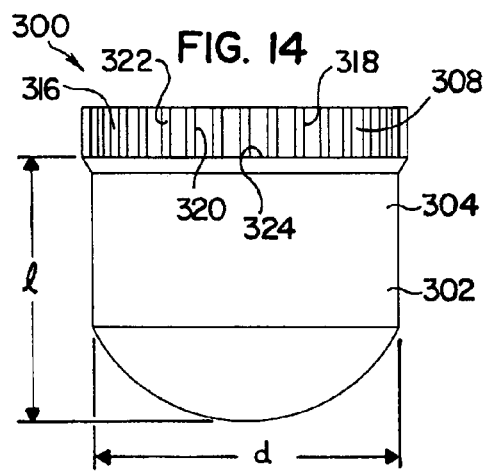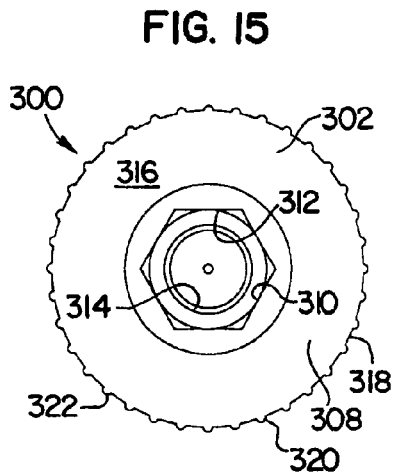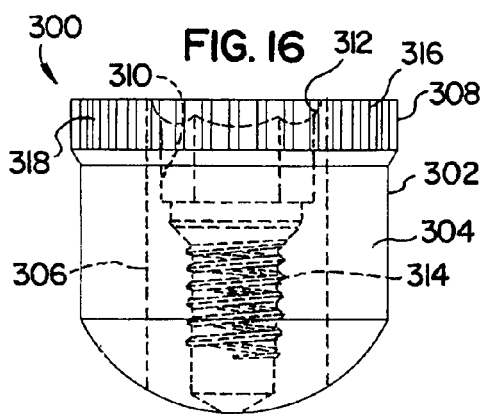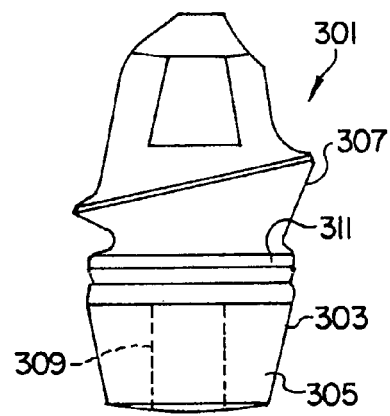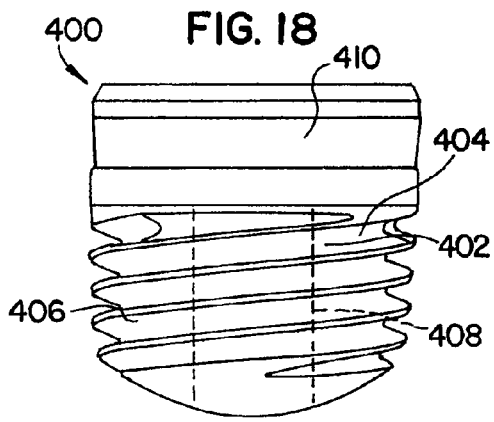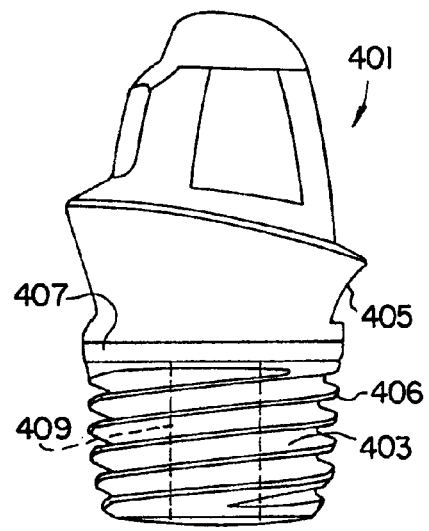

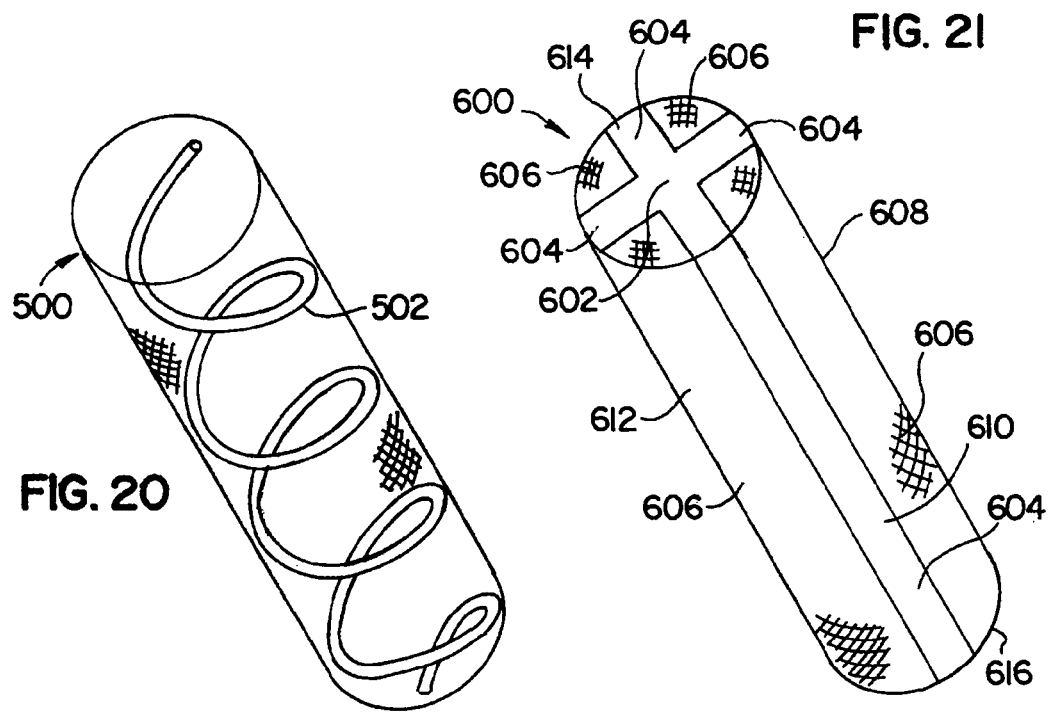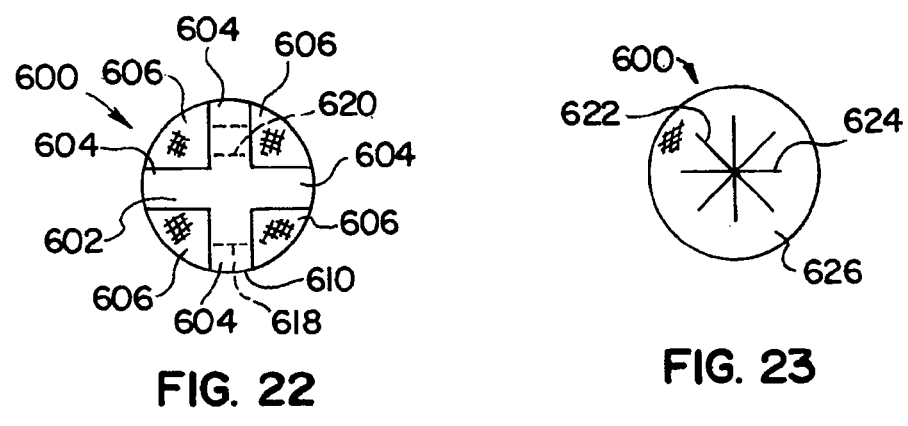

DENTAL IMPLANT FOR A JAW WITH REDUCED BONE VOLUME AND IMPROVED OSSEOINTEGRATION FEATURES

CROSS-REFERENCE TO RELATED APPLICATIONS

This application is a continuation-in-part of U.S. patent application Ser. No. 12/065,259, filed Feb. 22, 2008, now U.S. Pat. No. 8,075,312 which is a National Stage Application of International Application PCT/US2006/033893, with an international filing date of Aug. 30, 2006, which claims the benefit of U.S. Provisional Patent Application No. 60/712,577, filed Aug. 30, 2005, all of which are incorporated herein by reference in their entirety.

BACKGROUND OF THE INVENTION

1. Field of the Invention

The present invention relates to bone implants and, in particular, to a dental implant with improved osseointegration features.

2. Description of the Related Art

Dental implants are commonly used as anchoring members for dental restorations to provide prosthetic teeth at one or more edentulous sites in a patient's dentition at which the patient's original teeth have been lost or damaged. Typically, known implant systems include a dental implant made from a suitable biocompatible material, such as titanium. The dental implant is typically threaded into a bore which is drilled into the patient's mandible or maxilla at the edentulous site. The implant provides an anchoring member for a dental abutment, which in turn provides an interface between the implant and a dental restoration. The restoration is typically a porcelain crown fashioned according to known methods.

Many current dental implant surgeries are performed in two stages. In the initial or first stage, an incision is made in the patient's gingiva at an edentulous site, and a bore is drilled into the patient's mandible or maxilla at the edentulous site, followed by threading or impacting a dental implant into the bore using a suitable driver. Thereafter, a cap is fitted onto the implant to close the abutment coupling structure of the implant, and the gingiva is sutured over the implant. Over a period of several months, the patient's jaw bone grows around the implant to securely anchor the implant in the surrounding bone, a process known as osseointegration.

In a second stage of the procedure following osseointegration, the dentist reopens the gingiva at the implant site and secures an abutment and optionally, a temporary prosthesis or temporary healing member, to the implant. Then, a suitable permanent prosthesis or crown is fashioned, such as from one or more impressions taken of the abutment and the surrounding gingival tissue and dentition. In the final stage, the temporary prosthesis or healing member is removed and replaced with the permanent prosthesis, which is attached to the abutment with cement or with a fastener, for example.

Most patients, however, prefer to leave after the initial stage of surgery with some type of restoration in place. Furthermore, in many instances healing of both the soft and hard tissue can be improved if the implant is loaded after surgery. However, post-surgical loading of the implant, even if it is not the full load of occlusion, is sufficient to displace the implant, thus requiring some mechanism to achieve initial stability of the implant before osseointegration. One such mechanism can be a threaded dental implant. The threaded implant can achieve initial stability immediately after surgery because the threads resist any tension, twisting, or bending loads that the implant might be subjected to before biologic integration has taken place.

One disadvantage of the threaded implants, however, is that the surgical procedure is quite involved. A threaded implant needs to be turned into place, i.e., into the bore or socket of the jaw. This requires special tools, such as special ratchet wrenches and inserts. The torque required to place the threaded implant into the socket can also be high and sometimes tapping it into place is also needed, thus adding another step to the surgical procedure. Furthermore, the geometry of the thread establishes a relationship between the final vertical and rotational orientation of the implant and this can complicate implant placement by making optimal esthetics hard to achieve.

Press fit implants, on the other hand, are often preferred because the surgical procedure to place a press-fit implant is less complicated than that for a threaded implant. Press fit implants typically comprise a titanium cylinder. These types of cylindrical press fit implants, however, are not useful for immediate or early loading of the implant prior to osseointegration of the bone into the implant because they lack a mechanism to provide initial stability. Therefore, the current press fit design is not well suited for early and immediate load procedures that are currently very popular in dentistry. Thus, a press-fit dental implant is desired that provides adequate initial stability.

The known implants also have minimum size requirements to present sufficient surface area in contact with bone to form adequate initial and/or final stability, Thus, most common sizes for endosseous root form implants are about 7 mm to about 20 mm in length and about 3 mm to about 5 mm in diameter. In order for the jaw bone to have sufficient strength to hold the implant in place during mastication without damaging the jaw bone, generally, there should be adequate bone volume in addition to adequate bone density. For bone volume, there should be about 1-3 mm of bone on all sides of the implant. All sides refers to the apical, facial, and lingual directions from the implant and to the outer surface of the jaw, and in the distal and mesial directions from the implant and to the roots of adjacent teeth or implants.

Some dental patients, however, have a reduced depth alveolar ridge that does not provide sufficient bone volume to support the typical implant sizes. The reduced depth can be due to the patient's natural anatomy or due to bone atrophy caused by disease. The reduced alveolar ridge is often seen in edentulous or partially edentulous patients because the denture restorations they use do not load the jaw sufficiently to preserve bone. If bone is not stimulated by loading, the body finds other uses for the minerals that make up the tissue resulting in bone atrophy. The shallow ridge can result in a lessened dimension between the crest of the ridge and anatomic structure such as the mandibular canal or the sinus cavities.

Surgical bone augmentation procedures may be used before a dental implant is placed, such as bone grafting or sinus lifts, to increase the depth of the alveolar ridge. The procedures are typically invasive, however, requiring incisions to be made to harvest natural bone or to provide access to the sinus area to place grafting materials. Bone for grafting is often harvested from the chin or the hip, thus providing further discomfort to the patient. Also these procedures can add to the treatment time where healing of the graft must occur before the implant can be placed.

Alternatively, several short implants exist to treat these reduced depth areas. However, these implants are typically inadequate and prone to failure even though the implants may be made with known coatings or textures to promote osseointegration and increase initial stability. Thus, a dental implant is desired with structure for initial stability sufficient for placing the dental implant into a reduced bone volume region.

SUMMARY OF THE INVENTION

The present invention provides a dental implant which is made at least in part of a highly porous biomaterial such as porous tantalum for enhancing the osseointegration of the dental implant into surrounding bone. In one embodiment, a dental implant is provided which includes a core formed of titanium, for example, the core including a head portion having an abutment interface and a stem portion extending from the head portion. A porous tantalum sleeve is disposed about the stem portion and occupies a substantial portion of the implant/bone interface of the implant. After implantation of the implant, bone tissue may osseointegrate into the porous tantalum sleeve to anchor the implant in position within the surrounding bone. Other embodiments of implants are provided, each implant including at least a portion thereof formed of porous tantalum for improved osseointegration.

In one form thereof, the present invention provides a dental implant, including a core, and at least one porous tantalum portion connected to the core. The dental implant may further include a head portion including an abutment interface, and a stem portion projecting from the head portion. The porous tantalum portion may include a sleeve disposed about the stem portion of the core. The core may further include an abutment portion integrally formed with the core.

In another form thereof, the present invention provides a dental implant, including a body formed substantially of porous tantalum, and a bore extending at least partially into the body. The body may further include an outer surface and at least one rib extending from the outer surface.

In other alternative aspects of the embodiments described herein, the core may have a protrusion, such as a helical thread, extending though the porous body. In another alternative, the porous body may have reinforcement, such as reinforcing members or bars, extending within the body, and which may or may not be connected to a head portion of the dental implant. In one form, the head portion is configured to be press-fit onto the porous body.

In yet another form, the dental implant has a body with a porous metal portion for engaging bone, and an outer apical to coronal height and outer diameter that are both about 4 mm to about 6 mm. This structure permits the implant to be effective at reduced bone volume regions of a jaw.

BRIEF DESCRIPTION OF THE DRAWINGS

FIG. 3 is a partial cross-sectional view of a second embodiment of a dental implant, the dental implant including an implant body and an integral abutment portion;

FIG. 4 is a cross-sectional view of a third embodiment of a dental implant and an elevational view of an abutment;

FIG. 5 is a cross-sectional view of the dental implant of FIG. 4 and an elevational view of an anchor member;

FIG. 6 is a continuation of FIG. 5, showing deployment of the anchor member, and further showing an abutment;

FIG. 7 is cross-sectional view of a fourth embodiment of a dental implant and an elevational view of an abutment;

FIG. 8 is an elevational view of a fifth embodiment of a dental implant, and showing a thread protruding through a porous portion of the dental implant;

FIG. 9 is a cross-sectional view of a sixth embodiment of a dental implant, and showing a thread protruding through a porous portion of the dental implant;

FIG. 14 is a side elevational view of a tenth embodiment of a dental implant with a short and wide body;

FIG. 15 is an upper view of the dental implant of FIG. 14;

FIG. 16 is a side elevational view of the dental implant of FIG. 14 showing an internal bore;

FIG. 17 is a side elevational view of an eleventh embodiment of a dental implant including a press-fit implant body similar to FIG. 14 and further including an integral abutment portion;

FIG. 18 is a side elevational view of a twelfth embodiment of a dental implant showing a short and wide body having a threaded section;

FIG. 19 is a side elevational view of a thirteenth embodiment of a dental implant showing a short and wide body with threads and an integral abutment portion;

FIG. 20 is a transparent, perspective view of an alternative porous body with helical reinforcing for an implant;

FIG. 21 is a perspective view of another alternative body for an implant and with porous portions forming sectors throughout the body;

FIG. 22 is a transverse cross-sectional view of the implant body of FIG. 21; and FIG. 23 is an alternative transverse cross-sectional view for the implant body of FIG. 21.

Corresponding reference characters indicate corresponding parts throughout the several views. The exemplifications set out herein illustrate preferred embodiments of the invention, and such exemplifications are not to be construed as limiting the scope of the invention in any manner.

DETAILED DESCRIPTION

Figure 1:
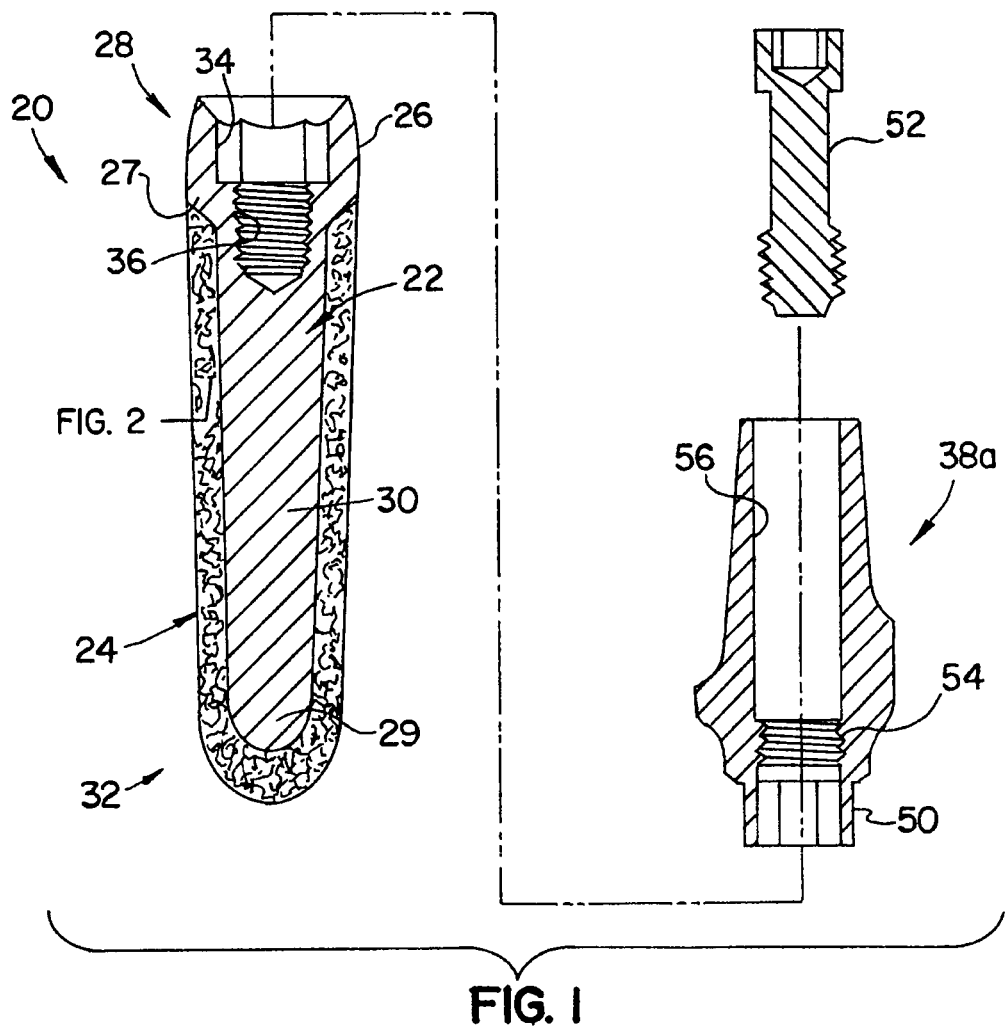
FIG. 1 is an exploded sectional view of a dental implant system including a dental implant with a core and a sleeve of porous tantalum, an abutment, and an abutment screw.
Figure 10:
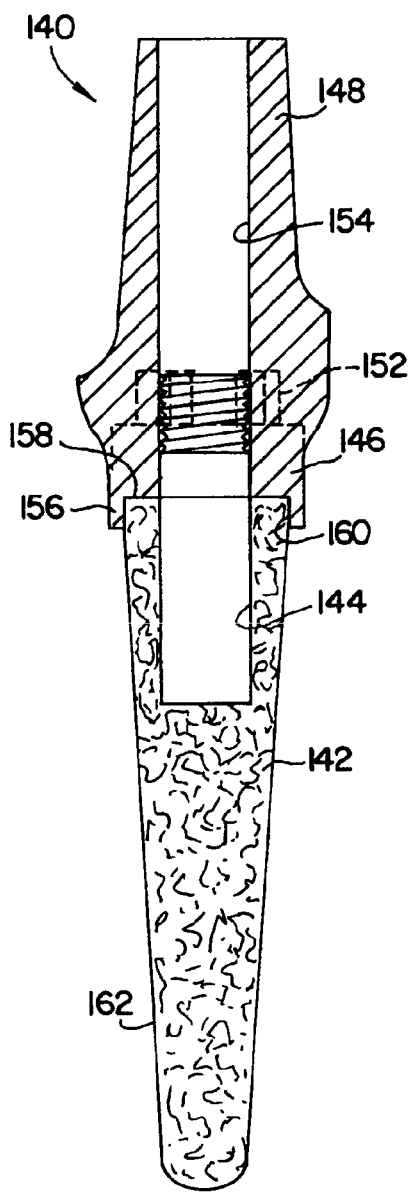
FIG. 10 is a cross-sectional view of a seventh embodiment of a dental implant, and further showing a head portion press-fit onto a porous implant body.

Referring to FIG. 1, there is illustrated a dental implant 20. Implant 20 may be cylindrical in shape or may be tapered in shape. Implant 20 generally includes a core 22 made of a suitable biocompatible material, such as titanium, and a sleeve 24 made of porous tantalum, as described below. Core 22 generally includes head portion 26 at a coronal, or proximal end 28 of implant 20, and stem portion 30 projecting from head portion 26 toward an apical, or distal end 32 of implant 20, wherein stem portion 30 is somewhat reduced in width or profile (cross-sectional) in comparison with head portion 26. Head portion 26 of core 22 additionally includes an abutment interface structure, shown herein as an internal hex 34 and an internally threaded bore 36 for attaching a dental abutment 38a to implant 20 in the manner described below. Although the abutment interface structure between implant 20 and abutment 38a is shown herein as an internal hex 34 within implant 20 which receives an external hex of abutment 38a as described below, the foregoing arrangement may be reversed. Also, many other types of implant/abutment interfaces are well known in the art, such as splines as represented in FIG. 10 in dashed line and shown in U.S. Pat. No. 5,449,291, the disclosure of which is hereby incorporated by reference, or other geometric shapes such as octagons, lobes, and other shapes.

Sleeve 24 is secured to core 22 in a suitable manner, such as via a cement or by sintering sleeve 24 to core 22, for example. As shown herein, sleeve 24 interfaces with the lower end 27 of head portion 26 of core 22, substantially encapsulates stem portion 30 of core 22, and extends distally below the end 29 of stem portion 30 of core 22. In this manner, a substantial portion of the bone interface or bone-contacting portion of implant 20 from proximal end 28 to distal end 32 thereof is formed by sleeve 24.

Sleeve 24 is formed of a highly porous biomaterial useful as a bone substitute and/or cell and tissue receptive material. An example of such a material is produced using Trabecular Metal™ technology generally available from Zimmer, Inc., of Warsaw, Ind. Trabecular Metal™ is a trademark of Zimmer Technology, Inc. Such a material may be formed from a reticulated vitreous carbon foam substrate which is infiltrated and coated with a biocompatible metal, such as tantalum, etc., by a chemical vapor deposition ("CVD") process in the manner disclosed in detail in U.S. Pat. No. 5,282,861, the disclosure of which is incorporated herein by reference. Other metals such as niobium, or alloys of tantalum and niobium with one another or with other metals may also be used.

Figure 2:
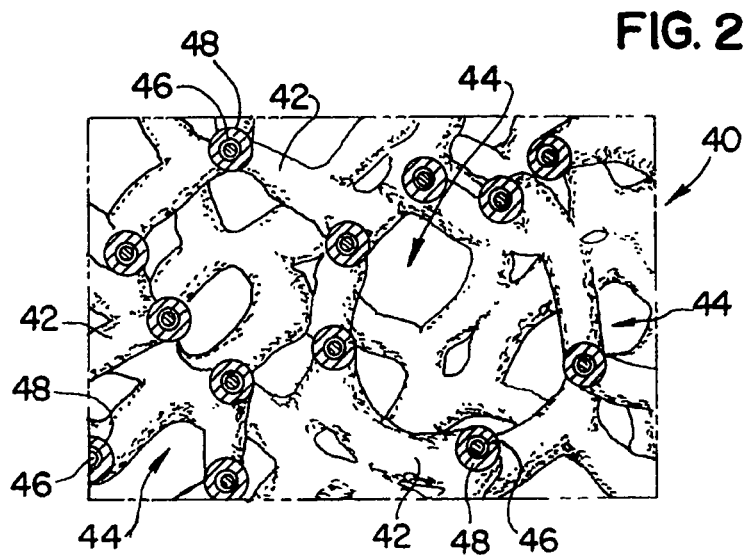
FIG. 2 is an enlarged fragmentary view of a portion of the porous tantalum sleeve of the implant of FIG. 1, showing the porous tantalum structure.

Generally, as shown in FIG. 2, porous tantalum structure 40 includes a large plurality of ligaments 42 defining open spaces 44 therebetween, with each ligament 42 generally including a carbon core 46 covered by a thin film of metal 48 such as tantalum, for example. The open spaces 44 between ligaments 42 form a matrix of continuous channels having no dead ends, such that growth of cancellous bone through porous tantalum structure 40 is uninhibited. The porous tantalum may include up to 75%-85% or more void space therein. Thus, porous tantalum is a lightweight, strong porous structure which is substantially uniform and consistent in composition, and closely resembles the structure of natural cancellous bone, thereby providing a matrix into which cancellous bone may grow to anchor implant 20 into the surrounding bone of a patient's jaw.

Porous tantalum structure 40 may be made in a variety of densities in order to selectively tailor the structure for particular applications. In particular, as discussed in the above-incorporated U.S. Pat. No. 5,282,861, the porous tantalum may be fabricated to virtually any desired porosity and pore size, and can thus be matched with the surrounding natural bone in order to provide an improved matrix for bone ingrowth and mineralization. This includes a gradation of pore size on a single implant such that pores are larger on an apical end to match cancellous bone and smaller on a coronal end to match cortical bone, or even to receive soft tissue in growth. Also, the porous tantalum could be made denser with fewer pores in areas of high mechanical stress. Instead of smaller pores in the tantalum, this can also be accomplished by filling all or some of the pores with a solid material which is described in further detail below.

To provide the additional initial mechanical strength and stability to the porous structure, the porous structure may be infiltrated with filler material such as a non-resorbable polymer or a resorbable polymer. Examples of non-resorbable polymers for infiltration of the porous structure may include a polyaryl ether ketone (PAEK) such as polyether ketone ketone (PEKK), polyether ether ketone (PEEK), polyether ketone ether ketone ketone (PEKEKK), polymethylacrylate (PMMA), polyetherimide, polysulfone, and polyphenolsulfone.

Examples of resorbable polymers may include Polylactide (PLA), Polyglycolic acid (PGA), polylactic co-glycolic acid (PLGA), polyhydroxybutyrate (PHB), polyhydroxyvalerate (PHV), Poly-L-lactide (PLLA), and copolymers thereof, polycaprolactone, polyanhydrides, and polyorthoesters. By providing additional initial mechanical strength and stability with a resorbable filler material, a titanium reinforcing implant core may not be required. The resorbable material would resorb titanium as the bone grows in and replaces it, which maintains the strength and stability of the implant. When the resorbable material is placed near the crest of the alveolar, the resorbable material forms a resorbable membrane to control the healing of soft and hard tissue. Since soft tissue grows and matures much faster than bone tissue, providing a membrane forms a barrier between the hard and soft tissue, thus restraining the soft tissue while the hard tissue heals and infiltrates the porous structure of the porous metal. These membranes then dissolve after a pre-determined amount of time so no extraneous material is left at the surgical site, and the soft tissue is free to grow against the implant.

The pores of the porous metal portion may also be filled with other materials such as bone growth proteins, antibiotics or human derived, animal derived or synthetic bone grafting materials. Each of the materials or combinations of any of these materials may provide a clinical advantage to the porous portion.

In use, implant 20 may be fitted into a bore (not shown) drilled into a patient's jaw bone at an edentulous site. In particular, implant 20 may be impacted or press-fitted into the bore to provide a firm initial seating of implant 20 into the bore. Thereafter, the bone tissue surrounding implant 20 may osseointegrate into the open spaces 44 of the porous tantalum of sleeve 24, thereby firmly anchoring sleeve 24 and implant 20 into the surrounding bone structure. At a later stage following osseointegration, an abutment 38a may be secured to implant 20 by fitting an external hex 50 of abutment 38a into internal hex 34 of core 22 of the implant, followed by threading abutment screw 52 through a screw retaining thread 54 within central bore 56 of abutment 38a and into threaded bore 36 of implant 20 to securely attach abutment 38a to implant 20. Thereafter, a temporary or permanent prosthesis (not shown) may be secured to abutment 38a in a known manner.

Optionally, implant 20, as well as the other implants described below, may have multiple textured surfaces as described in detail in U.S. Pat. No. 5,989,027, assigned to the assignee of the present invention, the disclosure of which is expressly incorporated herein by reference. Also, the implant may be formed with a rough surface such as fiber metal and/or cancellous-structured Titanium (CSTi™ made by Zimmer, Inc.) that may be applied on surfaces where the porous portion is not placed to further stimulate bone growth where desired.

As mentioned above, and in more specific detail, sleeve 24 of porous tantalum may have an increasing porosity from proximal end 28 toward distal end 32 of implant 20. Sleeve 24 could be formed of substantially solid, non-porous porous tantalum (i.e., the spaces 44 among ligaments 42 are made very small or eliminated) near proximal end 28 of implant 20 to provide a seal with the surrounding gingiva such that plaque or bacteria cannot lodge on or deposit within sleeve 24 near the gum line of the patient should the upper portion of sleeve 24 be exposed to the oral cavity. Alternatively, the surface of head portion 26 of core 22 could be formed of smooth, polished titanium to allow ready removal of bacterial plaque deposits by conventional oral hygiene techniques in the event that head portion 26 of implant 20 becomes exposed to the oral cavity. The porosity of the porous tantalum structure 40 of sleeve 24 could increase along the length of sleeve 24 toward distal end 32 of implant 20 to promote maximum bone ingrowth and osseointegration of implant 20 along implant 20 toward distal end 32 thereof. More specifically, the porous tantalum structure 40 of sleeve 24 could be formed with a gradient of increasing porosity from proximal end 28 toward distal end 32 of implant 20, wherein the open or void spaces 44 within the porous tantalum structure 40 become larger from proximal end 28 to distal end 32 of implant 20.

Also, sleeve 24 may be attached to core 22 of implant 20 in a manner wherein, after osseointegration of sleeve 24 into the surrounding bone, core 22 is slightly movable relative to sleeve 24 in order to dissipate forces which are imposed upon implant 20, such as mastication forces, for example. In one embodiment, sleeve 24 may be secured to core 22 via an adhesive material which is slightly compressible, such that when mastication or other forces are imposed upon head portion 26 of implant 20 via the prosthesis and abutment, head portion 26 and/or stem portion 30 of core 22 of implant 20 may move slightly relative to sleeve 24. In other embodiments, a compression ring, a spring, or another type of "shock absorbing" structure may be fitted between core 22 and sleeve 24 to allow for relative movement therebetween.

Referring to FIG. 3, there is illustrated a second embodiment of an implant. Implant 60 according to another embodiment of the present invention is shown as a "single-piece" implant which includes both an implant body and an integral abutment portion. Implant 60 may be formed of titanium, for example, and the body thereof includes proximal end 62 and distal end 64, with abutment portion 66 integrally formed with implant 60 and projecting from proximal end 62 of implant 60. Implant 60 includes sleeve 68 of porous tantalum disposed therearound, similar to implant 20 of FIG. 1 discussed above. Distal end 64 of implant 60 includes a thread 70 for initial anchoring or securement of implant 60 within a bore (not shown) drilled into the jaw bone of a patient. After initial anchoring of implant 60 into the bore via thread 70, a temporary prosthesis (not shown) may be secured to abutment portion 66 while a final prosthesis is fashioned. The bone-engaging portion of implant 60 may be generally cylindrical or may be tapered.

Referring to FIG. 4, there is illustrated a third embodiment of an implant. Implant 80 includes a generally cylindrical or bullet-shaped body portion 81 formed substantially entirely of porous tantalum. Implant 80 may also be tapered in shape. Implant 80 includes proximal end 82, distal end 84, and a central bore 86 extending from proximal end 82 partially into implant 80 towards distal end 84 thereof. Alternatively, as shown in FIG. 5 and discussed below, central bore 86 may extend entirely through implant 80 to distal end 84. Implant 80 may be screwed or torqued into a bore (not shown) drilled in a patient's jaw bone followed by allowing the surrounding bone tissue to osseointegrate into the porous tantalum of implant 80. When it is desired to secure abutment 38*b* to implant 80, threaded shaft 88 of abutment 38*b* may be threaded into central bore 86 of implant 80, wherein the threads of threaded shaft 88 of abutment 38*b* tap directly into the porous tantalum material surrounding central bore 86 to provide a rigid connection therebetween which is resistant to pull-out of abutment 38*b* from implant 80. Optionally, bore 86 of implant 80 may include a threaded metal sleeve in which threaded shaft 88 of abutment 38*b* may be threaded. Thereafter, osseointegration of surrounding bone tissue into and around the porous tantalum of implant 80 and threaded shaft 88 of abutment 38*b* further integrates implant 80 into the surrounding bone structure and also enhances the connection of abutment 38*b* to implant 80.

Referring to FIGS. 5 and 6, an anchor member 90 is shown which may optionally be used with implant 80. Anchor member 90 includes central shaft 92, a spring-loaded pivot joint 94, and a pair of anchor arms 96. After implant 80 is impacted into a bore (not shown) in a patient's jaw bone, anchor member 90 is driven through central bore 86 of implant 80 with anchor arms 96 in a retracted position as shown in FIG. 5, until anchor arms 96 clear distal end 84 of implant 80 externally of central bore 86. Thereafter, anchor arms 96 pivot at pivot joint 94 under the spring-loaded tension of pivot joint 94 to an extended position in which same are oriented in an opposed fashion perpendicular to the longitudinal axis of implant 80, such that the ends 98 of anchor arms 96 engage the bone within the bore in the patient's jaw bone. In this manner, anchor arms 96 provide an initial resistance to pull-out of implant 80 from the bore. Thereafter, after osseointegration of implant 80 into the surrounding bone tissue, abutment 38*b* may be secured by threading it into central bore 86 of implant 80 as described above. In addition to the spring-loaded anchor member embodiment described herein, other embodiments may be employed with other arrangements for providing additional anchoring to the implant.

Referring to FIG. 7, there is illustrated a fourth embodiment of an implant. Implant 100 includes a substantially cylindrical or bullet-shaped body 101 made substantially entirely of porous tantalum. Implant 100 also may be tapered in shape. Implant 100 includes proximal end 102, distal end 104, and a blind bore 106 extending partially into implant 100 from proximal end 102 thereof. Implant 100 additionally includes one or more ribs 108 protruding from the outer surface 110 thereof, wherein ribs 108 may be provided in the form of a single helical rib, or a plurality of annular ribs. In use, implant 100 is impacted into a bore (not shown) drilled into a patient's jaw bone, with ribs 108 engaging the surrounding bone to provide an initial resistance to pull-out of implant 100 from the bore before osseointegration of the implant 100 into the surrounding bone. Abutment 38*b* may be secured to implant 100 in the manner described above with respect to the embodiments of FIGS. 4-6 by threading threaded shaft 88 of abutment 38*b* directly into the porous tantalum surrounding blind bore 106 of implant 100. Optionally, blind bore 106 of implant 100 may include a threaded metal sleeve in which threaded shaft 88 of abutment 38*b* may be threaded.

Referring to FIGS. 8-9, there are illustrated a fifth and sixth embodiment, respectively. Implant 120 is constructed similarly to implant 60 (FIG. 3), while implant 130 is instructed similarly to implant 20 (FIG. 1). Thus, implants 120 and 130 have structures for connecting a porous body to abutments as described previously for implants 20 and 60. Also, implant 120 has a core 122 with a stem portion 123 (shown mainly in dashed line) extending within a preferably tantalum, porous portion or sleeve 126 similar to sleeve 68 on implant 60. The core 122 extends below the sleeve 126 to form cutting threads 127 like threads 70 on a distal end portion of the implant 60. Additionally, implant 130 has a porous sleeve 136 that covers both a stem portion 133 and a distal or apical end portion 131 of a core 132 similar to sleeve 24 of implant 20.

Here, however, the cores 122 and 132 have protrusions 124 and 134 that extend through respective sleeves 126 and 136 in order to facilitate cutting into the bone upon insertion of the implant into a bore on the jaw bone (not shown) and/or to aid in resistance to pull-out from the bore. The protrusions 124 and 134 preferably are helical ribs or threads 128 and 138 that extend respectively along stem portions 123 and 133. The threads 128 and 138 respectively extend through helical openings 125 and 135 on the sleeves 126 and 136. The helical threads 128 and 138 may extend past the porous sleeves 126 and 136 on the core of the implant, and may extend only in portions of the openings 125 and 135 on the sleeves 126 and 136 whether continuously or in separated segments along the helical path formed by the openings.

Referring to FIG. 10, there is illustrated a seventh embodiment of a dental implant. Dental implant 140 has a body 142 substantially made of a porous material, such as tantalum, similar to body 81 of the dental implant 80 (FIG. 4). The body 142 may include a bore 144 for attachment to an abutment connector 146. The bore 144 may be a blind bore or may have a threaded sleeve, as explained for body 81.

The abutment connector 146 covers a proximal or coronal surface 158 of the body 142 and may be provided with a number of different configurations to connect to an abutment. In one form, the abutment connector 146 may have an integral abutment and a threaded shank (not shown) received by bore 144, similar to abutment 38b for implant 80. Alternatively, the abutment connector 146 may have an integral abutment 148 similar to abutment 38a with a bore 154 for receiving a retaining screw similar to screw 52, both as shown in FIG. 1. In yet another alternative, the abutment connector 146 may be separate from the abutment and may have abutment interface structure including anti-rotational structure such as the spline structure 152 (shown in dashed line), the hex structure or others mentioned herein for engaging an abutment. These structures also may use a bore 154 for receiving the retaining screw. Whether the abutment connector 146 has an integral abutment or not, bore 154 on the abutment connector 146 aligns with bore 144 on the body 142 so that both bores can receive the retaining screw to secure the abutment connector 146 and abutment (if separate) to the body 142.

In order to create a tight fit or press-fit connection between the porous body 142 and the abutment connector 146, the connector 146 has a distally extending flange 156 that forms an opening 160. The flange 156 is preferably circular but may be other shapes to match the periphery of the coronal surface 158 of the body 142. So configured, the body 142 is connected to the abutment connector 146 by pressing the coronal end portion or surface 158 of the body 142 into opening 160. While the illustrated and preferred embodiments show that the press-fit connection may be provided in addition to other connecting structures between body 142 and connector 146, such as by retaining screw, threaded shank, reinforcing members (described below), fusion welding or adhesives, it should be understood that the press-fit connection may be the sole connection between the abutment connector 146 and the porous body 142.

In another aspect of this embodiment, body 142 is provided with a varying cross-sectional dimension so that a tapered outer surface 162 extends inwardly as it extends distally. The tapered surface 162 limits interference with the roots of adjacent teeth, and helps to redirect and dissipate compressive forces, generated from mastication, into transverse or lateral directions relative to a longitudinal axis of the implant. The tapered surface 162 also assists in aligning the implant with a bore on the jaw bone as it is being inserted into and through the bore.

Figure 11:
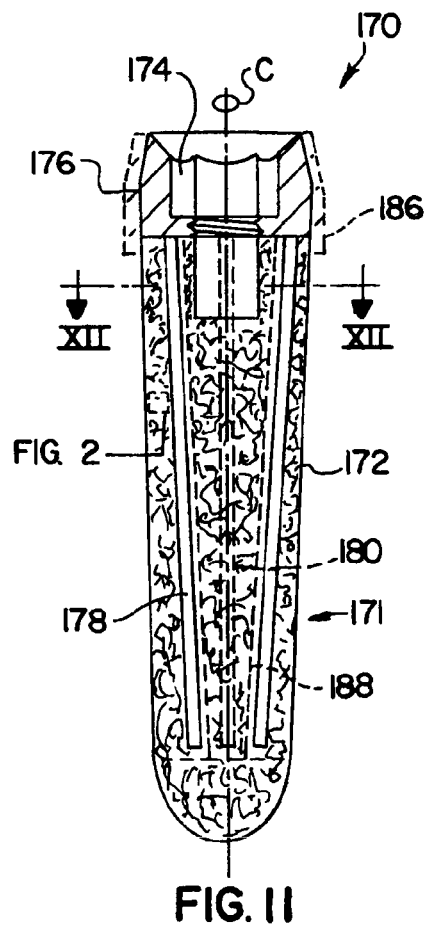
FIG. 11 is a cross-sectional view of a eighth embodiment of a dental implant, and including a porous portion of the dental implant with off center reinforcements.
Figure 12:
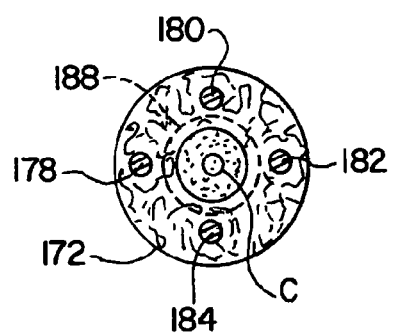
FIG. 12 is a cross-sectional view of the dental implant of FIG. 11 taken along the line XII-XII of FIG. 11.

Referring now to FIGS. 11-12, there are illustrated an eighth embodiment of an implant. Implant 170 has embedded reinforcing 171 to strengthen a substantially porous body 172. These reinforcements may be placed at the locations of greatest stress to provide the maximum amount of strengthening to the implant. These locations may be near the center or may be near the outer diameter of the implant. The body 172 has a material as described above for the body 81 of implant 80. Implant 170 also has an abutment connector 174 disposed on a coronal end 176 of the body 172. The abutment connector 174 is not particularly limited to a specific abutment-connecting configuration. For implant 170, reinforcement 171 includes a plurality of reinforcing members 178, 180, 182 and 184 generally aligned with, and preferably offset radially from, a central, longitudinal axis C of the body 172. In one form, the reinforcing members 178, 180, 182, 184 are elongated bars and may be made of the same or similar material to that of the abutment connector 174 and cores 22 and 62 mentioned above, which includes titanium. The members 178, 180, 182, 184 are uniformly spaced around the axis C and generally extend in a coronal-apical or superior-inferior direction. With this structure, the reinforcing members 178, 180, 182, and 184 dissipate compressive forces impacting on the implant from mastication. In the current embodiment, the reinforcing members 178, 180, 182, and 184 extend from the abutment connector 174 in order to provide further anchoring of the abutment connector 174 to the porous body 172. In this case, the members 178, 180, 182, and 184 may be integrally formed with, welded or otherwise connected to the abutment connector. This results in the direct transmission of impact forces from the abutment connector 174 to the reinforcing members 178, 180, 182, and 184, which further aids in dissipating the forces.

The abutment connector 174 also may be provided with a depending flange 186 (shown in dashed line) similar to flange 156, and the connector 174 may be appropriately sized, in order to provide a press-fit connection between the connector 174 and porous body 172, as described for implant 140.

As another alternative configuration, in addition to the reinforcing 171, the abutment connector 174 may be a portion of a central core 188 (shown in dashed line) that is provided to increase the strength of the implant 170. The reinforcing members 178, 180, 182, and 184 are generally aligned with, and spaced radially from, the core 188 and angled inward toward the core 188 proceeding from the proximate end toward the distal end.

Figure 13:
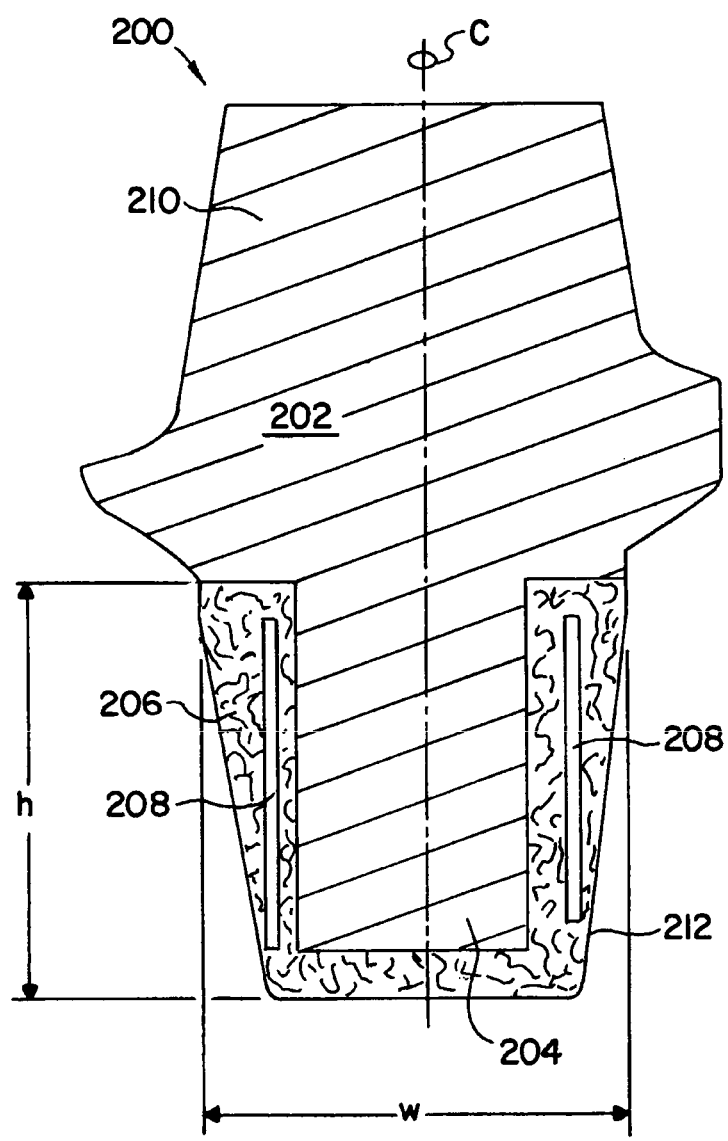
FIG. 13 is a cross-sectional view of a ninth embodiment of a dental implant, and showing an implant body with a central core and multiple off center cores.

Referring now to FIG. 13, there is illustrated another dental implant 200 with both a core and additional reinforcing. The implant 200 has an abutment connector 202 shown with an integral abutment 210 as one example abutment-connecting configuration. The abutment connector 202 has an enlarged central core 204 that extends into a porous body 206. The body 206 also has reinforcing members 208. The combination of reinforcing members 208 and core 204 provide substantial strength to compensate for significant bone loss in the jaw as occurs with geriatric patients. A heavily reinforced, short and wide implant 200 as measured on the outer surface of the porous body 206, is particularly suited for replacement of molars. Thus, in one example embodiment, the porous body 206 may provide outer dimensions of a width w of approximately 6 mm and a height h of approximately 6 mm. The reinforcing members 208 are disposed and oriented similarly to that of reinforcing members 178, 180, 182, and 184 in implant 170 mentioned above. In this embodiment, however, the reinforcing members 208 are not connected to the abutment connector 202 and do not angle inward.

It will be appreciated that other configurations for the reinforcing in FIGS. 11-13 may be provided than that shown including more or less reinforcing members. The reinforcing members may be provided in addition to a central core of a different material than the porous body or may be provided instead of such a central core. The reinforcing members may also generally extend in directions other than, or in addition to, a coronal-apical (or superior-inferior) direction. In one example form as shown in FIG. 20, a porous body 500 for an implant, similar to the porous bodies described above, has one or more helical reinforcement or bars 502 rather than, or in addition to, longitudinally extending reinforcement. The helical reinforcement 502 generally extends in a coronal-apical direction as it winds through the porous body 500. The helical reinforcement 502 may be attached to a head or abutment connector as explained above for reinforcement 171 on implant 170. The helical reinforcement 502, as well as reinforcement of other similar shapes, may be placed in any of the porous bodies described herein.

From the foregoing, it will be understood that the reinforcing for the porous material may include a core, whether a central core, off-center, solid, or entirely or partially hollow. The reinforcing may additionally or alternatively include off-center reinforcement members, whether or not a central core is present, and the reinforcing may protrude through the porous material, whether or not the core also protrudes through the porous material.

The porous body 206, as well as any of the porous bodies and porous sleeves described herein, may have a tapered outer surface 212 similar to tapered surface 162.

Referring to FIGS. 14-16, the properties of the porous metal described above provides a relatively high friction coefficient with bone so that a press-fit, short and wide implant with a porous metal portion as described previously has sufficient initial and final stability when the implant is placed into a reduced bone volume region on a jaw such as at a reduced alveolar ridge. More specifically, the struts of the porous material described above provide the porous material with a rough outer surface that sufficiently anchors the implant within a bore and against the jaw bone to resist forces caused by mastication. Since the implant is adequately immobile relative to the bone, rapid osseointegration onto and into the porous metal takes place, reducing the amount of time before biologic fixation augments the mechanical fixation.

In one example form, dental implant 300 has a body 302 with a porous metal portion 304 forming a round, endosseous root form shape for the implant 300. As illustrated, implant 300 is a two-stage surgery implant such that it should be disposed within bone along its entire length, although exposure of limited areas may be acceptable in some cases. Additionally, the implant 300 should be sufficiently wide to withstand mastication forces yet dimensioned to be adequately covered by at least about 1-3 mm of bone (and preferably more than about 2 mm) on the apical, distal, mesial, facial, and lingual sides of the implant including to adjacent implants and/or adjacent teeth. Furthermore, there should be sufficient vertical space coronally of the implant for the restorative components, yet the implant should also be placed sufficiently deep under the mucosa.

To satisfy these parameters, the porous metal portion 304 has an outer apical to coronal height or length l that is approximately 4 mm to approximately 6 mm long and an outer diameter d that is approximately 4 mm to approximately 6 mm in diameter. In another form, the height l and diameter d are approximately the same. In yet another form, the height l and diameter d are both about 6 mm.

The body 302 may be substantially made of the porous metal portion 304 or it may include an axially extending core 306 (shown in dashed line on FIG. 16) made of a non-porous material (titanium, for example) where the porous metal portion 304 forms a sleeve or external layer covering at least part of the core 306. In one form, the implant 300 has at least one longitudinal section of the implant 300 entirely or substantially formed of porous metal. If a core is present, this may include an apical end portion of the implant 300 substantially made of porous material when the core 306 ends just short of the apical end portion.

The body 302 can further comprise a coronal end or head portion 308 that has an abutment interface for connection to a separate abutment. As illustrated in FIG. 15, the abutment interface of the implant 300 can include an anti-rotational interface 310 which can be shaped like a hexagon or other polygonal shape. The anti-rotational interface 310 forms an opening 312 for receiving an apical end of an abutment as well as a fastening device, such as a pin or a screw, extending out of the apical end of the abutment. The anti-rotational interface 310 acts to prevent the abutment from rotating within the opening 312 on implant 300. The opening 312 also provides access to a coronally accessible, internally threaded bore 314 (as shown in dashed line in FIG. 16) to receive the pin or screw. The anti-rotational interface 310 and/or the internally threaded bore 314 may be formed by the porous metal portion 304 or the core 306 or partially by both.

When the porous metal portion 304 forms at least a substantial part of implant 300, implant 300 may not have sufficient strength to support the mastication loads applied to the implant. To strengthen the implant 300, a reinforcing collar 316 made of a material different than that of the porous metal, such as titanium, may form the head 308 of the implant 300. The collar 316 is disposed and configured to absorb and spread mastication forces, and forms a disc that at least partially, but here substantially, covers the coronal end 324 of the porous metal portion 304.

The collar 316 can also have an outer perimeter 318 with an array 320 of outwardly extending ribs 322 at least generally around the collar 316. The ribs 322 are elongated in a coronal-apical direction (i.e., extend axially). The ribs 322 provide the collar 316 with a less than entirely smooth, exterior, annular rim or surface that promotes bone growth at the crest of the alveolar ridge in which the collar 316 may be placed. In one form, the ribs 322 are uniformly placed around the entire collar 316, but other configurations for the ribs 322 and the shape of the collar 316 are contemplated. The collar 316 may also be the same material as the core 306 if present, and the collar 316 may be integrally formed with, or otherwise secured to, the core 306.

Referring to the embodiment shown in FIG. 17, a one-piece dental implant 301 has a body 303 that is the same or similar to body 302 and that has a porous metal portion 305 that at least forms the exterior of the body 303. The porous metal portion 305 may or may not encircle or partially cover a core 309 (shown in dashed line) similar to core 306. In this form, the implant 301 also has an abutment section 307 that supports a restoration. The abutment section 307 may be integrally formed with the porous metal portion 305. In this case, the abutment 307 has an integral endosseous collar portion 311 that is itself integral with the porous metal portion 305. Alternatively, the abutment section 307 is only integrally formed with non-porous collar portion 311 which may be similar to collar 316 described above. The collar portion 311 abuts or is otherwise connected to the porous metal portion 305. Additionally, or alternatively, the abutment section 307 may be integrally formed with the core 309. The abutment section 307 may be contoured as illustrated or may have a more cylindrical appearance.

In an alternative structure, instead of a full abutment section, implant 301 may be a single-stage surgery implant with an integral transgingival or emergence profile section that receives a separate abutment.

Referring to FIG. 18, a short and wide dental implant 400 has a body 402 with the same or similar structure to that of body 302 on implant 300 except here a porous portion 404 has exterior, porous threads 406 for adding further support and stability. Implant 400 may also have a non-porous strengthening collar 410, similar to collar 316, and core 408, similar to core 309, if present. While the implant 400 may be threaded into a bore in the jaw bone, in an alternative procedure, the implant 400 is press-fit into the jaw bone bore. The outer edges of the threads contact the bone and provide the initial stability. Over time, the bone will osseointegrate between the individual threads to rotationally lock the implant 400 in place.

Referring to FIG. 19, a one-piece dental implant 401 has exterior, porous threads 403 and the same or similar general structure as that of implant 400 (FIG. 18) except that it further includes an abutment section 405, as with implant 301 (FIG. 17), that is integral to a non-porous strengthening collar 407 and/or non-porous core 409, if present. It would be understood that the abutment section 405 could also be made integral to the porous threads 403.

It will also be understood that the short and wide implants 300, 301, 400, and 401 may take advantage of many of the design elements from any of the other implants described herein and vice-versa. For instance, it will be appreciated that the body 302 or 402 may include at least one reinforcing member extending through the porous metal portion, as disclosed with implant 200 (FIG. 13).

Turning to FIGS. 21-23, in another aspect of the implants, an implant body 600 has a generally cylindrical shape and includes an axially extending core 602, which can be made of a suitable biocompatible material as mentioned above, such as titanium, and may be attached to a head, abutment connector, or abutment portion of the implant as also described above. Here, however, the core 602 has a plurality of radially extending ribs 604, and separate porous bodies or sectors 606, formed of porous material as described above. The porous material is disposed between the ribs 604, extends radially to contact bone, and is attached to the core 602 as described above for the other implants.

A cylindrical outer surface 608 of the implant body 600 is formed by alternating distal surfaces 610 of the ribs 604 and surfaces 612 of the porous sectors 606 such that, in one form, the porous material extends less-than the full circumference around the implant body 600. In the illustrated form, the porous sectors 606 and ribs 604 extend from a coronal end portion 614 to an apical end portion 616 of the implant body 600, but this need not always be the case (e.g., the ribs or porous portion could stop short of the other of the porous portion and ribs in the coronal-apical direction). Similarly, while four porous sectors 606 are shown to be placed between four ribs 604, more or less ribs and separate porous sectors may be used.

Many other variations with a ribbed core are also contemplated. For example, the porous sectors 606 may not be entirely separated from each other, and may be linked together by one or more grooves 618 (shown in dashed line on FIG. 22) on the outer surface 610 of one or more of the ribs 604. Porous bridges may link adjacent porous sectors 606 through apertures 620 (also shown as dashed line on FIG. 22) in the ribs 604. Referring to FIG. 23, as yet another alternative, instead of ribs extending to the outer surface of the implant body 600, a core 622 may be provided with ribs 624 that extend short of the full diameter of the implant body 600. In this case, all, or an axial portion (in the coronal-apical direction), of one or more ribs 624 may be entirely buried within one or more porous bodies 626.

While the illustrated examples are dental implants, it will be understood that such structure, with bone-embedded sections of porous material such as porous metal or porous tantalum that have heights about the same as its width, or that have any of the other structures described herein, may be applied to implants for anywhere on an animal or human body.

While this invention may have been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A dental implant, comprising:
   a body having a porous metal portion for engaging bone and a coronal end including a polygonal shaped anti-rotational interface defining an opening configured for receiving an apical end of an abutment, the opening providing access to an internally threaded axially extending bore; and
   a reinforcing collar defining a head disposed toward the coronal end, wherein an exterior surface of the reinforcing collar includes an array of outwardly extending ribs elongated axially;
   the porous metal portion having an outer apical to coronal height of about 4 mm to about 6 mm and an outer diameter of about 4 mm to about 6 mm wherein the height and diameter are approximately the same to create a short and wide porous metal portion.

2. The dental implant of claim 1, wherein the outer height and the outer diameter are the same.

3. The dental implant of claim 1, wherein the outer height and outer diameter are both approximately 4 mm.

4. The dental implant of claim 1, wherein the porous metal portion forms the entire body.

5. The dental implant of claim 1, wherein the porous metal portion forms a majority of the body.

6. The dental implant of claim 1, wherein the implant generally defines a full circumference, and wherein the porous metal portion forms less than the full circumference of the implant.

7. The dental implant of claim 1, further comprising a resorbable material filling at least a portion of the porous metal portion.

8. The dental implant of claim 1, wherein the body has a core, and the porous metal portion forms a sleeve covering the core.

9. The dental implant of claim 1, wherein the body has at least one longitudinal section entirely formed of porous metal.

10. The dental implant of claim 1, wherein the porous metal includes tantalum.

11. The dental implant of claim 1, wherein the bore is formed by porous metal, and wherein the porous metal forms internal threads for connection to an abutment anchor.

12. The dental implant of claim 1, wherein the reinforcing collar is made of a material different than that of the porous metal and is disposed and configured for receiving mastication forces.

13. The dental implant of claim 12, wherein the reinforcing collar includes titanium.

14. The dental implant of claim 1, wherein the reinforcing collar further comprises a less than entirely smooth exterior surface to promote bone growth against the exterior surface.

15. The dental implant of claim 1, wherein the array of outwardly extending ribs extends around at least a portion of the reinforcing collar and is made of a same material as the core.

16. The dental implant of claim 1, wherein the body has an outer surface formed by the porous metal, at least a portion of the porous metal forming threads for engaging bone.

17. The dental implant of claim 16, wherein the implant can be press-fit into the bone.

18. The dental implant of claim 1, wherein the body further comprises an abutment portion.

19. The dental implant of claim 1, wherein at least one reinforcing member extends through the porous metal portion.

20. The dental implant of claim 19, wherein the reinforcing member extends in a helical arrangement through the porous metal portion.

21. The dental implant of claim 1, wherein the dental implant comprises a single porous metal portion.

22. A prosthetic device, comprising:
a bone-embedded section having a generally porous tantalum portion covering at least an exterior of the bone-embedded section, the porous tantalum portion having an outer height approximately the same as an outer diameter of the porous tantalum portion,
wherein the bone-embedded section includes a coronal end including a polygonal shaped anti-rotational interface defining an opening configured for receiving an apical end of an abutment, the opening providing access to an internally threaded axially extending bore, and
wherein the coronal end includes a reinforcing collar defining a head, an exterior surface of the reinforcing collar including an array of outwardly extending ribs elongated axially.

23. The prosthetic device of claim 22, wherein the bone-embedded section is an endosseous section.

24. The prosthetic device of claim 23, wherein the endosseous section further comprises a core made of a material different from the material forming the porous tantalum portion.

25. A prosthetic device, comprising:
an endosseous section having a generally porous tantalum portion with a porous material and covering at least an exterior of the endosseous section, the porous tantalum portion having an outer height of approximately 4 mm to approximately 6 mm and an outer diameter of approximately 4 mm to approximately 6 mm;
a coronal end of the endosseous section including a polygonal shaped anti-rotational interface defining an opening configured for receiving an apical end of an abutment, the opening providing access to an internally threaded axially extending bore;
a reinforcing collar defining a head disposed toward the coronal end, wherein an exterior surface of the reinforcing collar includes an array of outwardly extending ribs elongated axially; and
at least one reinforcing member that is other than the central core of the prosthetic device and having an outer surface embedded within the porous metal tantalum portion so that the entire outer surface is in contact with the porous material.

26. An implant, comprising:
a body having a porous metal section with porous material for engaging bone and including a coronal end including a polygonal shaped anti-rotational interface defining an opening configured for receiving an apical end of an abutment, the opening providing access to an internally threaded axially extending bore, the coronal end including a reinforcing collar defining a head, wherein an exterior surface of the reinforcing collar includes an array of outwardly extending ribs elongated axially; and
at least one reinforcing bar having an outer surface embedded within the porous metal section so that the entire outer surface is in contact with the porous material and wherein the at least one reinforcing bar is other than a central longitudinal core of the implant.

27. The implant of claim 26, wherein the porous metal section includes tantalum.

28. The implant of claim 26, wherein the at least one reinforcing bar is helical.

29. The implant of claim 26, wherein the body generally defines a longitudinal axis and, wherein the at least one reinforcing bar comprises an elongate body generally defining a longitudinal axis that is not the same as the longitudinal axis of the body.

30. An implant body for engaging bone comprising:
a longitudinal axis and a circumference transversely extending around the longitudinal axis;
a coronal end including a polygonal shaped anti-rotational interface defining an opening configured for receiving an apical end of an abutment, the opening providing access to an internally threaded axially extending bore;
a reinforcing collar disposed toward the coronal end, wherein an exterior surface of the reinforcing collar includes an array of outwardly extending ribs elongated axially;
a plurality of non-porous, radially extending ribs having alternating distal surfaces circumferentially spaced from each other around the circumference; and
at least one porous portion disposed circumferentially between the radially extending ribs around the circumference.

31. The implant of claim 30, further comprising at least two porous portions, and wherein the radially extending ribs entirely separate the porous portions from each other.

32. The implant of claim 30, wherein the at least one porous portion includes tantalum.

33. A dental implant, comprising:
a body having a porous metal portion for engaging bone and a coronal end including a polygonal shaped anti-rotational interface defining an opening configured for receiving an apical end of an abutment, the opening providing access to an internally threaded axially extending bore;
the porous metal portion having an outer apical to coronal height of about 4 mm to about 6 mm and an outer diameter of about 4 mm to about 6 mm wherein the height and diameter are approximately the same to create a short and wide porous metal portion;
wherein at least one reinforcing member extends in a helical arrangement through the porous metal portion.

34. An implant, comprising:
a body having a porous metal section with porous material for engaging bone and including a coronal end including a polygonal shaped anti-rotational interface defining an opening configured for receiving an apical end of an abutment, the opening providing access to an internally threaded axially extending bore, and
at least one helical reinforcing bar having an outer surface embedded within the porous metal section so that the entire outer surface is in contact with the porous material and wherein the at least one helical reinforcing bar is other than a central longitudinal core of the implant.

* * * * *